US009674880B1

(12) United States Patent
Egner et al.

(10) Patent No.: US 9,674,880 B1
(45) Date of Patent: *Jun. 6, 2017

(54) METHOD AND APPARATUS FOR A SMART VEHICLE GATEWAY WITH CONNECTION CONTEXT AWARE RADIO COMMUNICATION MANAGEMENT AND MULTI-RADIO TECHNOLOGY

(71) Applicant: Dell Products, LP, Round Rock, TX (US)

(72) Inventors: Will A. Egner, Cedar Park, TX (US); Liam B. Quinn, Austin, TX (US)

(73) Assignee: Dell Products, LP, Round Rock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,182

(22) Filed: Jan. 14, 2016

(51) Int. Cl.
| | |
|---|---|
| *H04M 1/00* | (2006.01) |
| *H04W 76/02* | (2009.01) |
| *H04W 4/02* | (2009.01) |
| *G05B 15/02* | (2006.01) |
| *H04W 88/06* | (2009.01) |

(52) U.S. Cl.
CPC .......... *H04W 76/021* (2013.01); *G05B 15/02* (2013.01); *H04W 4/028* (2013.01); *H04W 88/06* (2013.01)

(58) Field of Classification Search
USPC .............. 455/550.1, 552.1, 41.1–41.3, 456.1
See application file for complete search history.

(56) References Cited

U.S. PATENT DOCUMENTS

| | | |
|---|---|---|
| 7,013,145 B1 | 3/2006 | Centore, III |
| 8,666,048 B2 | 3/2014 | Beerse et al. |
| 9,088,859 B2 | 7/2015 | Egner et al. |
| 9,119,039 B2 | 8/2015 | Egner et al. |
| 9,143,926 B2 | 9/2015 | Egner et al. |
| 9,167,591 B2 | 10/2015 | Egner et al. |
| 9,210,714 B2 | 12/2015 | Egner et al. |
| 2004/0192341 A1 | 9/2004 | Wang et al. |
| 2005/0041696 A1 | 2/2005 | Pekonen |

(Continued)

*Primary Examiner* — Fayyaz Alam
(74) *Attorney, Agent, or Firm* — Prol Intellectual Property Law, PLLC; H. Kenneth Prol

(57) ABSTRACT

An information handling system functioning as a smart vehicle gateway includes a wireless adapter for communicating with a plurality of wireless links and a storage device for storing a spatial-temporal user profile comprising wireless device usage trend data for a plurality of locations where the smart vehicle gateway has operated. The smart vehicle gateway further includes a positional detector to detect a location of the smart vehicle gateway and an application processor to correlate the wireless device usage trend data to a location and to determine a list of optimal wireless service carriers and available wireless protocols at the location based on a mobile wireless traffic report with a spatial-temporal radio frequency profile indicating signal quality for the plurality of wireless links and the wireless device usage trend data for the location. The smart vehicle gateway application processor selects an international mobile subscriber identity (IMSI) for one of the optimal wireless links for an electronic subscriber identity module (eSIM) programmable to switch between multiple available wireless service carriers and then switches the wireless adapter to the selected optimal wireless link.

20 Claims, 14 Drawing Sheets

(56) References Cited

U.S. PATENT DOCUMENTS

| | | |
|---|---|---|
| 2005/0215290 A1 | 9/2005 | Wakabayashi et al. |
| 2006/0268849 A1 | 11/2006 | Larsson et al. |
| 2007/0060130 A1 | 3/2007 | Gogic et al. |
| 2009/0181695 A1 | 7/2009 | Wirola et al. |
| 2009/0279502 A1* | 11/2009 | Zheng ............... H04W 36/0033 370/331 |
| 2009/0319348 A1 | 12/2009 | Khosravy et al. |
| 2010/0202376 A1 | 8/2010 | Zhu et al. |
| 2010/0220665 A1 | 9/2010 | Govindan et al. |
| 2011/0143761 A1 | 6/2011 | Uusitalo et al. |
| 2012/0057569 A1 | 3/2012 | Xie et al. |
| 2013/0023274 A1* | 1/2013 | Meredith ............... H04W 48/18 455/450 |
| 2014/0066117 A1* | 3/2014 | Egner ................... H04W 4/003 455/513 |
| 2014/0094208 A1* | 4/2014 | Egner ................. H04W 72/085 455/513 |
| 2014/0106753 A1* | 4/2014 | Narasimhan .......... H04W 36/14 455/436 |
| 2015/0350877 A1* | 12/2015 | Li ......................... H04W 8/183 455/558 |
| 2016/0135040 A1* | 5/2016 | Suzuki .................... H04W 8/26 455/422.1 |
| 2016/0182737 A1* | 6/2016 | Suzuki ................ H04M 15/852 455/408 |

* cited by examiner

METHOD AND APPARATUS FOR A SMART VEHICLE GATEWAY WITH CONNECTION CONTEXT AWARE RADIO COMMUNICATION MANAGEMENT AND MULTI-RADIO TECHNOLOGY

CROSS REFERENCE TO RELATED APPLICATIONS

This application is related to U.S. patent application Ser. No. 14/099,686, entitled "Method and Apparatus for Connection Context Aware Radio Communication Management with Predictive Mobile Path," filed on Dec. 6, 2013, now issued U.S. Pat. No. 9,119,039, issued Aug. 25, 2015, which is a continuation-in-part of U.S. patent application Ser. No. 13/604,906, entitled "Method and Apparatus for Connection Context Aware Radio Communication Management," filed on Sep. 6, 2012, now issued U.S. Pat. No. 9,088,859, issued Jul. 21, 2015, the disclosures of which are hereby expressly incorporated by reference in their entirety. elated subject matter is contained in the following co-pending applications:

U.S. application Ser. No. 14/532,343, filed Nov. 4, 2014, entitled "Method and Apparatus for Unified Communication System Involving Context Aware Radio Communication Management for Multiple User Devices," invented by Will A. Egner et al., and assigned to the assignee hereof.

U.S. application Ser. No. 14/532,455, filed Nov. 4, 2014, entitled "Collaborative Method and System to Improve Carrier Network Policies with Context Aware Radio Communication Management," invented by Will A. Egner et al., and assigned to the assignee hereof.

U.S. application Ser. No. 14/804,317, filed Jul. 20, 2015, entitled "Method and Apparatus for Connection Context Aware Radio Communication Management," invented by Will A. Egner et al., and assigned to the assignee hereof.

U.S. application Ser. No. 14/834,091, filed Aug. 24, 2015, entitled "Method and Apparatus for Connection Context Aware Radio Communication Management for a Predicted Mobile Path," invented by Will A. Egner et al., and assigned to the assignee hereof.

U.S. application Ser. No. 14/886,603, filed Oct. 19, 2015, entitled "Method and Apparatus for Determining Optimized Wireless Link Selection for a Mobile Device Along a Predicted Path," invented by Will A. Egner et al., and assigned to the assignee hereof.

U.S. application Ser. No. 14/960,596, filed Dec. 7, 2015, entitled "Method and Apparatus for Predicting Mobile Device Wireless Link Quality of Service Requirements Along a Predicted Path," invented by Will A. Egner et al., and assigned to the assignee hereof.

U.S. application Ser. No. 14/820,387, filed Aug. 6, 2015, entitled "Method and Apparatus for Optimizing End to End Radio Communication Management for Users with Multiple Devices," invented by Will A. Egner et al., and assigned to the assignee hereof.

U.S. application Ser. No. 14/541,562, filed Nov. 14, 2014, entitled "Method and System for Optimizing Shared Spectrum Utilizing Context Aware Radio Communication Management," invented by Will A. Egner et al., and assigned to the assignee hereof.

FIELD OF THE DISCLOSURE

The present disclosure generally relates to a method and apparatus for a radio resources communication management system to adapt to context and usage of communication channels with a smart vehicle gateway.

BACKGROUND

As the value and use of information continues to increase, individuals and businesses seek additional ways to process and store information. One option is an information handling system. An information handling system generally processes, compiles, stores, or communicates information or data for business, personal, or other purposes. Technology and information handling needs and requirements can vary between different applications. Thus information handling systems can also vary regarding what information is handled, how the information is handled, how much information is processed, stored, or communicated, and how quickly and efficiently the information can be processed, stored, or communicated. The variations in information handling systems allow information handling systems to be general or configured for a specific user or specific use such as financial transaction processing, airline reservations, enterprise data storage, internet of things (IOT) monitoring and communications, or global communications. In addition, information handling systems can include a variety of hardware and software resources that can be configured to process, store, and communicate information and can include one or more computer systems, graphics interface systems, data storage systems, and networking systems. Information handling systems can also implement various virtualized architectures. Data communications among information handling systems may be via networks that are wired, wireless, optical or some combination.

BRIEF DESCRIPTION OF THE DRAWINGS

It will be appreciated that for simplicity and clarity of illustration, elements illustrated in the Figures are not necessarily drawn to scale. For example, the dimensions of some elements may be exaggerated relative to other elements. Embodiments incorporating teachings of the present disclosure are shown and described with respect to the drawings herein, in which.

The use of the same reference symbols in different drawings indicates similar or identical items.

DETAILED DESCRIPTION OF THE DRAWINGS

The following description in combination with the Figures is provided to assist in understanding the teachings disclosed herein. The description is focused on specific implementations and embodiments of the teachings, and is provided to assist in describing the teachings. This focus should not be interpreted as a limitation on the scope or applicability of the teachings.

Figure 1:
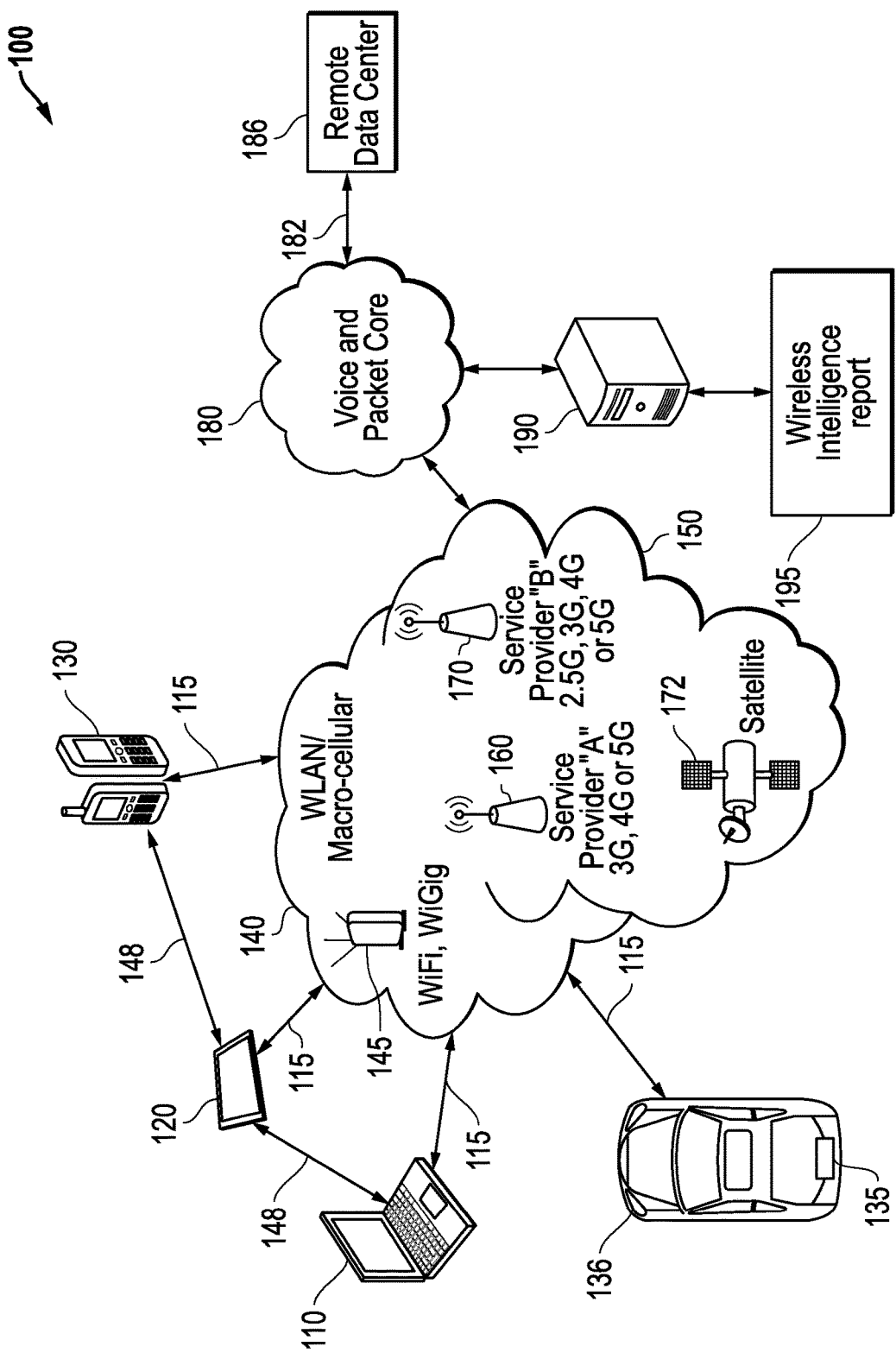
FIG. 1 is a block diagram of a network environment offering several communication protocol options according to an embodiment of the present disclosure.

FIG. 1 illustrates a network 100 that can include one or more information handling systems. For purposes of this disclosure, the information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, an information handling system may be a personal computer, a PDA, a mobile information handling system, a consumer electronic device, a network server or storage device, a switch router or other network communication device, or any other suitable device and may vary in size, shape, performance, functionality, and price. The information handling system may include memory, one or more processing resources such as a central processing unit (CPU) or hardware or software control logic, and operates to execute code. Additional components of the information handling system may include one or more storage devices that can store code, one or more communications ports for communicating with external devices as well as various input and output (I/O) devices, such as a keyboard, a mouse, and a video display. The information handling system may also include one or more buses operable to transmit communications between the various hardware components.

In a particular embodiment, network 100 includes networked mobile information handling systems 110, 120, and 130, wireless network access points, and multiple wireless connection link options. Systems 110, 120, and 130 represent a variety of computing resources of network 100 including client mobile information handling systems, data processing servers, network storage devices, local and wide area networks, or other resources as needed or desired. As specifically depicted, systems 110, 120, and 130 may be a laptop computer, tablet computer, or smart phone device.

Network 100 may additionally include a smart vehicle gateway 135 associated with vehicle 136. Smart vehicle gateway 135 may be an information handling system with wireless communication capability as well as processing capability. In some example embodiments, smart vehicle gateway 135 may be a vehicle computing system and may interface with processors, memory, and functionality of one or more on-board vehicle computing systems. In other embodiments, smart vehicle gateway 135 may be a separate information handling system which may operate as a wireless network access point.

These user mobile information handling systems 110, 120, and 130, and smart vehicle gateways 135 may access a wireless local area network 140, or they may access a macro-cellular network 150. For example, the wireless local area network 140 may be the wireless local area network (WLAN), a wireless personal area network (WPAN), or a wireless wide area network (WWAN). Since WPAN or Wi-Fi Direct Connection 148 and WWAN networks can functionally operate similar to WLANs, they may be considered as wireless local area networks (WLANs) for purposes herein. Components of a WLAN may be connected by wireline or Ethernet connections to a wider external network. For example, wireless network access points 145 may be connected to a wireless network controller and an Ethernet switch. Wireless communications across wireless local area network 140 may be via standard protocols such as IEEE 802.11 Wi-Fi, IEEE 802.11ad WiGig, IEEE 802.15 WPAN or similar wireless network protocols. Alternatively, other available wireless links within network 100 may include macro-cellular connections 150 via one or more service providers 160 and 170. Service provider macro-cellular connections may include 2G standards such as GSM, 2.5G standards such as GSM EDGE and GPRS, 3G standards such as W-CDMA/UMTS and CDMA 2000, 4G standards such as WiMAX, LTE, and LTE Advanced or upcoming 5G standards. Additional macrocellular connections may also be available through satellite networking systems. It is understood that satellite network systems may utilize macro-cellular broadband protocols similar to the ones listed above or may utilize proprietary satellite communication protocols. Other options may be available as well including macro-cellular options available via base station or other wireless uplink radio connections made available in airborne vehicles such as aircraft, drones, hot air balloons, or similar flying vehicles for certain applications.

Smart vehicle gateway 135 may also interface, via local wireless adapter, with user mobile information handling systems similar to those depicted at 110, 120, and 130 and which are located within vehicle 136. Smart vehicle gateway 135 may similarly interface, via local wireless adapter, with IoT sensors and devices as well as mobile devices and vehicle computing systems which are located within vehicle 136. Interfacing with devices within vehicle 136 may be done using a local vehicle network such as Wi-Fi, Wi-Fi Direct, WPAN, Bluetooth Zigbee or another similar local network protocols to wirelessly communicate with mobile devices or sensors within or nearby the vehicle 136. Located "within a vehicle" or "associated with" a vehicle 136 hereinafter will refer to information handling systems, IoT devices such as sensors, smart vehicle gateways 135, or other computing devices inside of a vehicle, integrated with a vehicle, attached to a vehicle, or nearby a vehicle and which may access the local vehicle network and the smart vehicle gateway local wireless adapter.

The voice and packet core network 180 may contain externally accessible computing resources and connect to a remote data center 186. The voice and packet core network 180 may contain multiple intermediate web servers or other locations with accessible data (not shown). Connection 182 between the wireless network 140 and remote data center 186 may be via Ethernet or another similar connection to the world-wide-web, a WAN, a LAN, another WLAN, or other network structure. Such a connection 182 via WLAN access point/Ethernet switch 145 to the external network is a backhaul connection. The access point 145 may be connected to one or more wireless access points in the WLAN before connecting directly to a mobile information handling system or may connect directly to one or more mobile information handling systems 110, 120, and 130. Alternatively, mobile information handling systems 110, 120, and 130 and smart vehicle gateway 135 may connect to the external network via base station locations at service providers such as 160 and 170. These service provider locations may be network connected via backhaul connectivity through the voice and packet core network 180.

Remote data center 186 may include web servers or resources within a cloud environment. For example, remote data centers can include additional information handling systems, data processing servers, network storage devices, local and wide area networks, or other resources as needed or desired. Having such remote capabilities may permit fewer resources to be maintained at the client mobile information handling systems 110, 120, and 130, at smart vehicle gateway 135, or at computing systems or IoT devices within vehicle 136 allowing streamlining and efficiency within those devices. Similarly, remote data center 186 permits fewer resources to be maintained in other parts of network 100.

In an example embodiment, the cloud or remote data center 186 may run hosted applications for systems 110, 120, and 130 and smart vehicle gateway 135. This may occur by establishing a virtual machine application executing software to manage applications hosted at the remote data center 186. Mobile information handling systems 110, 120, and 130 and smart vehicle gateway 135 are adapted to run one or more applications locally, and to have hosted applications run in association with the local applications at remote data center 186. The virtual machine application may serve one or more applications to each of user mobile information handling systems 110, 120, and 130 or smart vehicle gateway 135. Thus, as illustrated, systems 110, 120, and 130 or smart vehicle gateway 135 may be running applications locally while requesting data objects related to those applications from the remote data center 186 via wireless network. For example, an electronic mail client application may run locally at system 110. The electronic mail client application may be associated with a host application that represents an electronic mail server. In another example, a data storage client application such as Microsoft Sharepoint may run on system 120. It may be associated with a host application running at remote data center 186 that represents a Sharepoint data storage server. In a further example, a web browser application may be operating at system 130. The web browser application may request web data from a host application that represents a hosted website and associated applications running at remote data center 186.

In yet another example embodiment, a smart connect manager application may be run at a smart vehicle gateway 135 to determine wireless connection access options based on vehicle location and relevant context and anticipated communication and data needs in accordance with embodiments disclosed herein. Smart connection manager at a smart vehicle gateway 135 may request or send data objects or information to or from an application running at a remote data center 186 or another location such as a context aware radio resource management system remote server 190. Context aware radio resource management system remote server 190 may operate a context aware radio resource management system application according to the present disclosures. Similarly, remote access may be available to a remote database with wireless intelligence reports 195.

To communicate within the network 100, the systems 110, 120, and 130 and smart vehicle gateway 135 each have a wireless interface module or wireless adapter, hereinafter referred to as a wireless adapter. System 110 includes a wireless adapter, system 120 includes a wireless adapter, system 130 includes a wireless adapter, and smart vehicle gateway 135 includes a wireless adapter. The wireless adapters are operable to provide a wireless radio frequency interfaces, or wireless links, 115 to transmit and receive voice and data between the respective systems 110, 120, 130, and smart vehicle gateway 135 and one or more external networks via wireless network 140 or 150.

Although wireless links 115 are shown connecting wireless adapters to wireless networks 140 or 150, actual wireless communication may link through a wireless access point 145 or a service provider tower such as that shown with service provider A 160 or service provider B 170. A wireless link may also be made between the wireless adapter and another mobile information handling system in a WPAN or Wi-Fi Direct Connection 148. Systems such as 110, 120, and 130 may also have wireless adapters for communicating with a smart vehicle gateway 135 such as when located within a vehicle. Again, WPAN, Wi-FI, Wi-Fi Direct, Bluetooth Zigbee or other local wireless communication protocols may be used within the vehicle 136. Since one aspect of the disclosed embodiments involves selection of wireless links by a context aware radio resource management system, no particular wireless link selection is depicted in FIG. 1.

The wireless adapters can represent add-in cards, wireless network interface modules that are integrated with a main board of respective systems 110, 120, and 130 or integrated with another wireless network interface capability, or any combination thereof. In an embodiment the wireless adapters may include one or more radio frequency subsystems including transmitters and wireless controllers for connecting via a multitude of wireless links. In an example embodiment, a mobile information handling system or smart vehicle gateway 135 may have a transmitter for Wi-Fi or WiGig connectivity and one or more transmitters for macrocellular communication. The radio frequency subsystems include wireless controllers to manage authentication, connectivity, communications, power levels for transmission, buffering, error correction, baseband processing, and other functions of the wireless adapters.

The radio frequency subsystems of the wireless adapters may measure various metrics relating to wireless communication. For example, the wireless controller of a radio frequency subsystem may manage detecting and measuring received signal strength levels, bit error rates, signal to noise ratios and other metrics relating to signal quality and strength. In one embodiment, a wireless controller may manage one or more radio frequency subsystems within a wireless adapter. The wireless controller also manages transmission power levels which directly affect radio frequency subsystem power consumption. To detect and measure power consumption by a radio frequency subsystem, the radio frequency subsystem may implement current and voltage measurements of power that is directed to operate a radio frequency subsystem. The voltage and current provides power measurement in milliwatts. Energy consumed may be calculated from sample measurements by taking average power measured over a duration of transmission. In an alternative embodiment of power measurement, counter registers may be used to estimate power consumed during transmissions. Energy measurement may be a sampled during a count cycle. In this case, a sample energy measurement per count is multiplied into a count for operation of a radio subsystem. In this way, power consumption may be estimated.

The wireless adapters may be capable of connecting via a WLAN 140 or a macro-cellular network (WWAN) 150 and service provider 160 or 170 in a variety of the wireless standards as described above. Each of the wireless adapters for client mobile information handling systems 110, 120, and 130 and smart vehicle gateway are uniquely identified on network 100 via one or more unique identifiers permitting authentication and access. For example, the wireless device can each be identified by one or more Subscriber Identity Modules (SIM), one or more programmable electronic SIMs, one or more of a media access control (MAC) address, an Internet protocol (IP) address, a world wide name (WWN), or another unique identifier such as a user name and password, as needed or desired. For a smart vehicle gateway 135, it may be advantageous to provide for switching between eSIM identifications to permit selection of optimal wireless links to be on a home network, rather than while "roaming." A smart connection manager operating on a smart vehicle gateway 135 may switch an eSIM to permit election of a new international mobile subscriber identity (IMSI) for election to communicate on a different service provider network selected from multiple available wireless service carriers. In one embodiment, the wireless adapter may be used to establish a plurality of wireless links in accordance with disclosures herein. In another embodiment, a plurality of eSIMs may be available to provide for establishing a plurality of wireless links on more than one wireless service carrier in accordance with embodiments disclosed herein.

Traditional carrier SIMs have a single fixed IMSI and are limited in terms of alternative wireless service carrier selection based on individual negotiated carrier roaming relationships. Often these roaming connections may be more expensive. Additionally, these roaming connections may be less efficient in that link switching to the desired wireless service carrier from the home carrier may require routing to a carrier link location to enable connection. In an alternative embodiment, the radio frequency subsystems of a wireless adapter may contain individual subscriber identity module (SIM) profiles for each technology service provider and their available protocol. These multiple SIM profiles on the mobile information handling system may be provided by one broker such as an MVNO, or by multiple service providers. In many instances, a full set of SIM profiles available from a pool of IMSIs may be checked out and provided. The system may have an application processor for the wireless adapter capable of switching between SIM profiles at the information handling system. The switching between SIM profiles and accessing the service providers may be conducted by information handling systems 110, 120, 130 or smart vehicle gateway 135. Thus, a wireless link recommendation from a context aware radio resource management system would not need to be transmitted to network broker server system 190. Information handling systems 110, 120, 130 or smart vehicle gateway 135 may select a SIM profile for a recommended service provider and protocol and seek direct access. In the case of a network broker server system, billing and other coordination of SIM profile options may be managed by a broker such as an MVNO. The context aware radio resource management system is described further below.

eSIMs allow additionally flexibility in selecting radio connection beyond single carrier and subscriber IMSI systems since an eSIM may be programmable for multiple IMSIs. eSIMs can be used to overcome international roaming restrictions, for example, by enabling smart vehicle gateways to operate within a region as a local carrier on significantly reduced connection rates. eSIMs also offer convenience of reprogramming to a home (or anchor) carrier SIM without having to remove and replace a physical SIM as with traditional carrier SIMs. It further avoids wear and tear on the system such as breakage of a SIM cradle.

Association of a user and a wireless interface module of an information handling system such as a smart vehicle gateway may be made via communications across a networking control plane. For example, a user information handling system may be associated with a user via communication with a database such as Home Subscriber Server (HSS), Active Directory or similar database. This database may reside in the voice and packet core network 180, at a base station at 160 or 170, or elsewhere in the external network.

The wireless adapters may operate in accordance with any wireless data communication standards. To communicate with wireless local area network 140, standards including IEEE 802.11 WLAN standards, IEEE 802.15 WPAN standards, WWAN such as 3GPP or 3GPP2, or similar wireless standards may be used. The wireless LAN network 140 may provide connectivity via Wi-Fi or WiGig for example. The wireless network 140 may have a wireless mesh architecture in accordance with mesh networks described by the above wireless data communications standards or similar standards. Wireless links 115 may also connect to the external network via a WPAN, WLAN or similar wireless switched Ethernet connection. The wireless data communication standards set forth protocols for communications and routing via access point 145, as well as protocols for a variety of other operations. Other operations may include handoff of client devices moving between nodes, self-organizing of routing operations, or self-healing architectures in case of interruption.

Wireless links 115 may connect to a macro-cellular wireless network 150 via one of the service providers 160 or 170. In the depicted example, service provider A 160 may provide wireless data connectivity via a 3G or 4G protocol. Service provider B 170 may offer connectivity via a 2.5G, 3G or 4G protocol. Any combination of macro-cellular wireless connectivity is possible for each or both of the service providers. The connection quality of service (QOS) and speed of wireless links 115 may vary widely depending on several factors including the service provider bandwidth, the number of mobile information handling systems and users in a location, and other factors. Quality of service impacts energy consumption and efficiency of a mobile information handling system communicating wirelessly. Thus, selection of a wireless link may depend on assessment of the link radio frequency conditions. Radio frequency conditions for wireless links will evolve over time. Differences in wireless link QOS or efficiency will also vary minute-by-minute, hourly, daily, weekly or monthly or during even longer periods. Thus, assessment may need to be regular. This is particularly true for a smart vehicle gateway 135 where vehicle travel may alter conditions depending on location.

Wireless link conditions will vary depending on the type of service likely to be requested by the mobile information handling system. For example, voice communication may be most efficient on a 2G wireless protocol. Voice communication on 4G may be more costly in terms of time required for authentication and connectivity negotiation or in terms of transmission power requirements. Data services relating to messaging and SMTP email may have the lowest power cost on 2.5G protocols due to the simplest access barriers there. Higher level data services requiring greater wireless bandwidth may more efficiently use recently implemented protocols. For example, audio streaming may be optimal for 3G protocols. Video streaming and HTTP web browsing may be best suited to 4G protocols and much less efficient at lower protocols which are not designed to accommodate large data throughput.

As the protocols become more advanced, additional registration and initialization for data becomes costly from a processing and power consumption standpoint. This is balanced against the capabilities of the more advanced protocols to handle data transfers. More complicated communication protocols result in greater processing time and authentication/connection message exchange. More robust processor or controller operation and longer delays for transmitter or receiver circuits consume power. On the other hand, certain protocol advancements are designed to make data transfers quicker and more efficient. Thus for example, the 4G protocol may generally consume more power during operation than 2.5G for voice communications, but less power for high volume data transfers.

For this reason, the mobile information handling system operating context can play an important role in determining wireless link conditions and efficiency from a power consumption standpoint. Information about wireless link connection quality and capacity for a service to be used can be advantageous in optimizing communication channel selection. In most cases, transmission or reception via a macro-cellular network 150 base station at a service provider 160 or 170 will take more power than communication via WLAN such as Wi-Fi. Among macro-cellular systems, energy consumption generally, but not in all circumstances, increases at each advancement of technology protocol from 2G to 4G. Plus, increased traffic levels on an advanced macro-cellular protocol may slow down in comparison to an older technology with less active traffic. Additional future macro-cellular protocols are contemplated as well. Those protocols may require additional energy demands of mobile information handling systems.

Factors impacting energy consumption include switching and signaling during communication access, setup, and authentication. Additional factors that impact energy consumption include control communications, latencies, transmission/reception, and switching for the wireless link. As described above, these factors can be specific to the type of wireless service being requested, whether voice, messaging, SMTP, Audio, Video, HTTP or other service types. It can also be specific to the mobile information handling system used. Certain protocols may not be available on some mobile information handling systems. In each instance, radio frequency transmission subsystems and controllers operate and consume device power. Based on these numerous factors, the system of the present embodiment may automatically switch between radio network technologies or service providers to optimize radio frequency conditions, traffic conditions, device power consumption, cost, or any of the above. Selection of a wireless service provider and technology protocol may generally depend on the optimal wireless technology used for a service requested, the radio frequency conditions of a link, traffic conditions for the wireless link, and availability of a link. Wireless service provider may also be referred to as wireless service carrier herein. Technology protocol is also referred to as wireless protocol in some instances herein as well.

Information handling systems 110, 120, 130, and smart vehicle gateway 135 may connect to the network 140 or 150 via an initial default wireless link with one of the service providers 160, 170 or via a WPAN, Wi-Fi, or WiGig connection.

The default wireless link allows the mobile information handling systems 110, 120, and 130 to communicate with the network and in particular with a context aware radio resource management system remote server 190 in one embodiment. The context aware radio resource management system remote server 190 may interface with a network broker system server on the same server location or another server location as described in embodiments herein. The context aware radio resource management system remote server 190 and/or mobile information handling systems 110, 120, and 130 and smart vehicle gateway 135 leverage information from a Wireless Intelligence Report system database 195 and may determine optimal access to a macro-cellular service provider or WLAN.

Optimal, as used herein, refers to those wireless links or service carriers/providers that meet a minimum threshold or set of thresholds for providing wireless service as determined with the context aware radio resource management system. For example, threshold factors such as radio frequency QoS, wireless traffic levels, power consumption requirements, or cost of service, among other factors of a wireless link may determine thresholds which, when assessed in view of expected wireless data and communication usage, are selected as sufficient by the context aware radio resource management system. The context aware radio resource management system may decide that at a remote server 190, or at a local wireless device such as a smart vehicle gateway 135 or other mobile information handling system.

The network broker server system that interfaces with the context aware radio resource management system may be operated as a mobile virtual network operator (MVNO), a wireless service provider wholesaler, a mobile network operator (MNO), or similar type of network broker. For example, in some embodiments, the network broker server system may have contractual bulk access to network services from a variety of mobile network operators or service providers. The contractual bulk access may include pools of IMSIs available for check out to users.

In another example embodiment, the context aware radio resource management system, whether remote or local, may interface with one or more eSIMs to select an IMSI for use with a wireless service provider. The eSIM provides for a wireless adapter to switch between IMSIs and permits a user to elect from among several wireless service providers and protocols as a "home" network. For example, a smart connect manager operating on a smart vehicle gateway 135 may trigger an IMSI switch via one or more eSIMs.

With access to network services from multiple service providers, the context aware radio resource management system may enable access or switch access for information handling systems 110, 120, and 130 among the available service providers. By way of example, a smart connect manager may select an IMSI from among wireless service carriers 160 and 170 as a home network for the smart vehicle gateway 135, and thus for information handling systems or IoT sensors and other IoT devices within vehicle 136.

Information handling systems 110, 120, and 130 or smart vehicle gateway 135 may be multiband capable via the wireless adapters therein. Antenna system frequency and radio protocols for a service provider may be adjusted by way of software programming of transmitter/receiver systems of the wireless adapters in mobile information handling systems 110, 120, 130 and smart vehicle gateway 135. Information handling systems 110, 120, 130 and smart vehicle gateway 135 may be multiband capable via these tunable antennas enabling a wireless adapter to target specific bands depending on the selected service provider and wireless protocol.

The context aware radio resource management system remote server 190 may also access aggregated Wireless Intelligence Report 195 about the performance of service providers 160 or 170 and the various wireless protocols they have made available. The aggregated Wireless Intelligence Reports 195 may be accumulated or crowd sourced from multiple handsets operating on a given network or networks. This feature will be described further below. In one embodiment, Wireless Intelligence Reports 195 may partly comprise mobile wireless traffic reports and may also include spatial-temporal radio-frequency profiles as discussed herein. Mobile wireless traffic reports relate to wireless link conditions including for mobile broadband connections via WWAN, WLAN connections, satellite connections, and other wireless connection options. Wireless Intelligence Reports, or relevant portions thereof, may be transmitted to or stored with mobile information handling systems 110, 120, and 130 or with a smart vehicle gateway 135 in some embodiments. In an example, relevant data for each mobile information handling system 110, 120, and 130, or for a smart vehicle gateway 135 to locations, types of data and communications, or times of operation may be transmitted for local storage. In another aspect, the aggregated Wireless Intelligence Report 195 may be stored on the context aware radio resource management system remote server 190 itself. The selection of a service provider and protocol by the context aware radio resource management system remote server 190 for an information handling system seeking a wireless link will be according to a recommendation received from a context aware radio resource management system agent running on the information handling system. The wireless link recommendation may be a weighted list of service provider options and protocols. It may be submitted by the context aware radio resource management system operating in a smart vehicle gateway 135 or on mobile information handling systems 110, 120, and 130 in some of the described embodiments. Alternatively, the context aware radio resource management system agent could run remotely on the network broker server systems or at a remote data center and use a default wireless link until an optimal wireless link is selected and the smart vehicle gateway 135 or mobile information handling system is switched.

Figure 2:
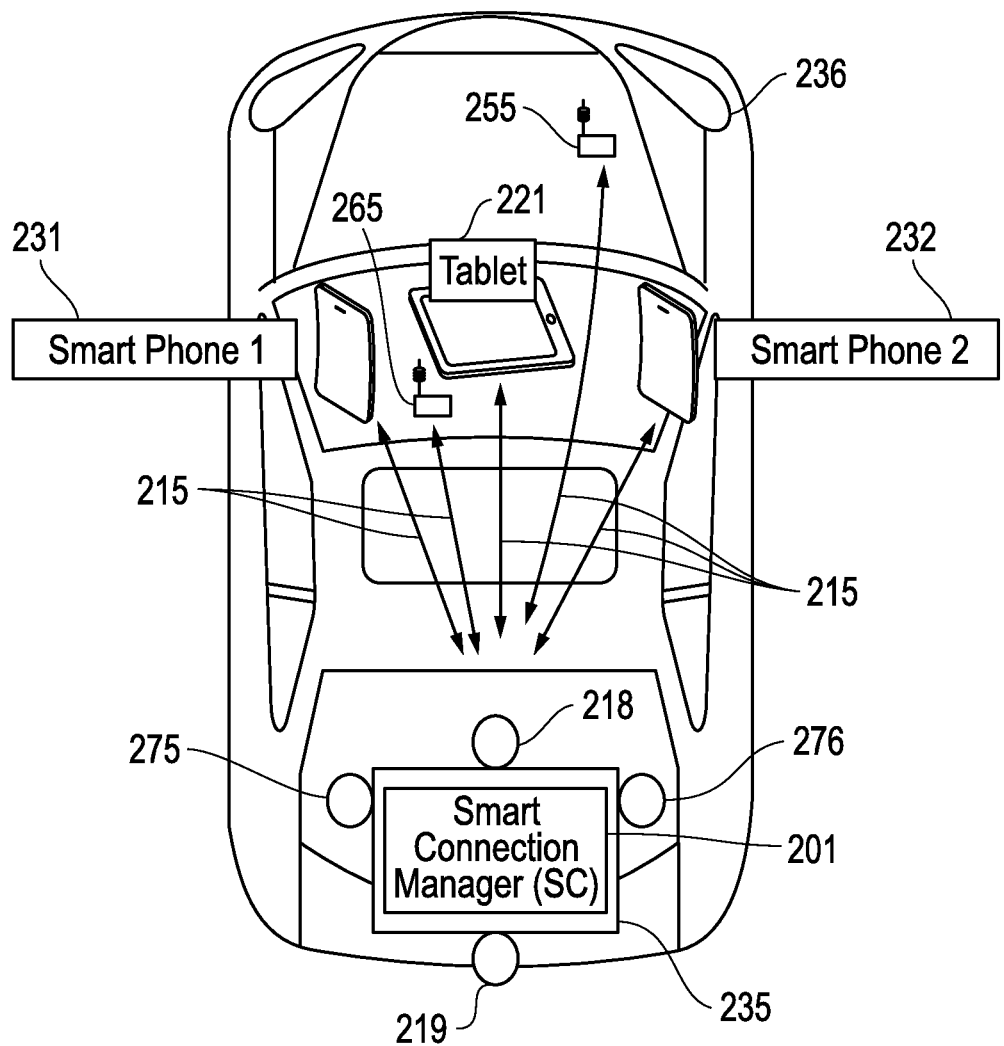
FIG. 2 is a block diagram of a smart vehicle gateway according to an embodiment of the present disclosure.

FIG. 2 illustrates a vehicle 236 having an information handling system functioning as a smart vehicle gateway 235. Power for the smart vehicle gateway 235 may be available from various sources including power from the vehicle. Other embodiments may use battery systems to provide power to the smart vehicle gateway. Vehicle 236 may have one or more mobile information handling system within. For example, vehicle 236 may have a first smart phone 231 or a second smart phone 232, or tablet computing system 221 located within the vehicle 236.

Vehicle 236 may also have one or more IoT sensors 255, 265. IoT sensors 255 may be part of the vehicle and may include sensor for engine temperature, speed, fuel consumption, combustion, cabin temperature, chemical sensors and or similar vehicle operational parameters. IoT sensors 265 may involve personal or vehicle payload monitoring sensors. IoT sensors 265 may also include human telemetry sensors for drivers or pilots or may relate to temperature, chemical, lighting, or other sensors relating to vehicle payloads or atmosphere conditions within a vehicle. Other IoT sensors may provide driver road conditions such has average speed for transportation reporting, vehicle tire pressure, and traction along vehicle braking systems. Such IoT sensors may be used for assisting neighboring car travel and for avoidance of traffic accidents in an example embodiment. In other embodiments, IoT radar system sensors can add to enhance an ability of a vehicle to detect and avoid collisions. With the smart vehicle gateway, high wireless connection reliability is improved without cabling and additional weight. In an example embodiment, the variety of IoT devices, such as sensors, allow a company with a fleet of vehicles to better manage transport logistics at a remote command center.

Figure 3:
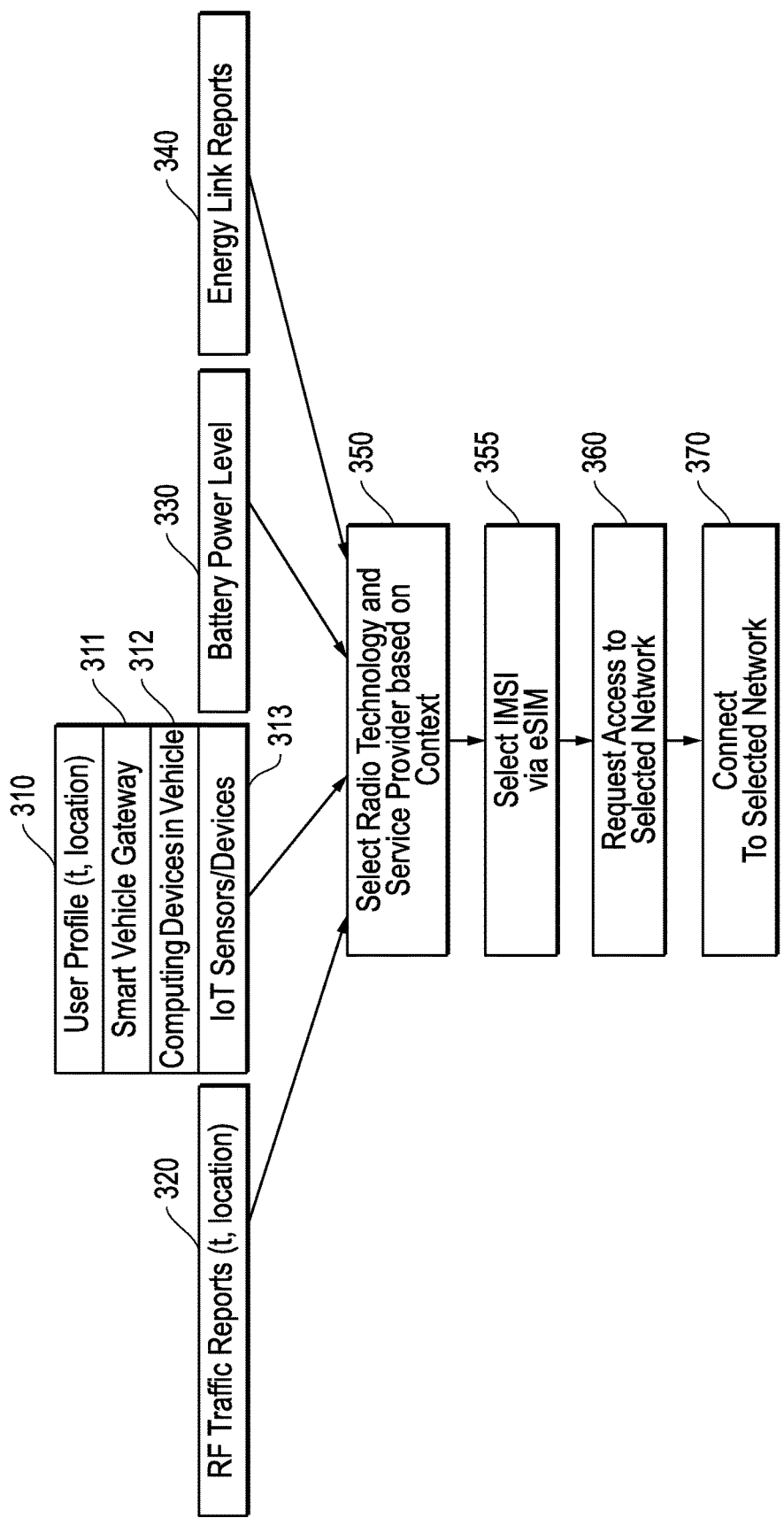
FIG. 3 is a flow diagram illustrating a method of connecting to a wireless network using a context aware radio resource management system according to an embodiment of the present disclosure.

Each mobile information handling system 221, 231, or 232 may have a local wireless link 215 with a smart vehicle gateway 235. Several example protocols are discussed above. In FIG. 3, Wi-Fi is shown as one example connection. Similarly, IoT sensors 255 and 265 may have a local wireless link 215 with smart vehicle gateway 235 as well. The smart vehicle gateway 235 has a local wireless adapter 218 for communication via the local wireless links 215 to devices in the local vehicle network.

The smart vehicle gateway 235 also has a WWAN wireless adapter with an eSIM 275. eSIM of WWAN wireless adapter 275 is a SIM system having software switchable subscriber identity modules for changing an international mobile subscriber identity (IMSI) associated with the smart vehicle gateway 235. By switching international mobile subscriber identity associated with the WWAN wireless adapter 275 of the smart vehicle gateway, the smart vehicle gateway may select to alter its home network upon selection of a wireless service carrier and a wireless protocol. The smart vehicle gateway 235 has a smart connection manager 201 which may be software code or firmware code executed by a processor or controller. Smart connection manager 201 operates in connection with a context aware radio resource management system executable code operating on processors locally or remotely to switch wireless adapters to a selected wireless link from a list of optimal wireless links. For example, smart connection manager 201 may execute instructions to issue commands to an eSIM to switch IMSI's to utilize a wireless service carrier as a home network for purposes of selecting a wireless link from a list of optimal wireless links provided via the context aware radio resource management system.

In one example embodiment, smart vehicle gateway 235 may have a second WWAN wireless adapter with a second eSIM 276. In some embodiments, it is also understood that more than two wireless adapters with separate eSIMs is contemplated. With at least two WWAN wireless adapters each with switchable eSIMs 275 and 276, the smart connection manager 201 of a smart vehicle gateway 235 may establish two or more wireless links to a WWAN for efficient and seamless communication to the WWAN depending on the wireless conditions of a location of vehicle 236. The two or more wireless links may thus be established across the same wireless service carrier or across different wireless service carriers. Each wireless carrier may be utilized as a home network. Further, plural wireless protocols may be established for the plurality of wireless links to improve options for vehicle communication with the WWAN. This may be beneficial for vehicle travel across borders or between ranges of service provider network systems to avoid roaming which may cause increased costs and potential delays. In this way, the smart connection manager 201 of the smart vehicle gateway 235 may leverage the context aware radio resource management system with mobile wireless traffic reports and wireless usage trend data to opportunistically select from established wireless links to a WWAN.

The available open wireless links will have been established from among the optimal wireless links by the context aware radio resource management system. In an aspect, this will have been done with additional factors relating to wireless device usage trend data for the smart vehicle gateway 235 taken into account. In another aspect of the present disclosure, selection of a wireless link to a WWAN for the smart vehicle gateway 235 may be established from among the optimal wireless links by the context aware radio resource management system further taking into account information handling systems 221, 231, and 232 or IoT sensors 255, 265 determined to be within vehicle 236. Wireless device usage trend data for information handling systems 221, 231, and 232 or IoT sensors 255, 265 may impact the selection of the WWAN wireless links by the smart connection manager 201 for example.

In some embodiments, the smart vehicle gateway 235 will also have a satellite radio adapter for satellite based communications. For example, the satellite based communication may be used in some embodiments for connection to the context aware radio resource management system remote server 190. A high priority satellite link may be used to obtain wireless intelligence reports including mobile wireless traffic reports and even wireless device usage trend data stored remotely. In other examples, a context aware radio resource management system remote server 190 may perform the analysis of a mobile information handling system or the smart vehicle gateway 235 to provide a list of optimal wireless links via satellite for use by a smart connection manager 201. In yet other embodiments, voice, data, and other communications via satellite may be considered as an option from among the upstream wireless link options available to the smart vehicle gateway 235.

In some embodiments, when a smart vehicle gateway is set to establish a wireless link to a WWAN from a smart vehicle gateway, the IMSI options may be provided from a network broker system. In an example embodiment, the network broker system may provide IMSIs to fleets of vehicles. The network broker system has pools of IMSIs that may be checked out for a wireless adapter based on location. The pools of IMSIs at the network broker system include multiple wireless service carriers and several IMSIs from each wireless service carrier are licensed to the network broker system. For example, an IMSI pool may include four wireless service provider IMSI options in one embodiment. Previously, network broker systems would send all available IMSIs options, one for each wireless service provider available, via over-the-air (OTA) activation to a user's wireless adapter. Thus, no analysis was conducted to determine which wireless service carriers were to be used. It is beneficial for a wireless adapter such as a smart vehicle gateway to limit the IMSI options from a network broker system and limit the IMSIs checked out to it. A context aware radio resource management system may be used to filter the IMSI wireless service provider options checked out from the pool of IMSIs at the network broker system.

With a smart filtering or screening of the IMSIs requested from a network broker system, the network broker system may be able to carry a fewer number of IMSIs to supply the pools for checkout by users. This may in turn reduce costs at the network broker by requiring fewer licenses to the IMSIs. That cost savings may also reduce costs for a user.

In addition, the context aware radio resource management system will request only IMSIs for optimal wireless link options as determined by link ratings described in the present disclosure. Thus, when a smart vehicle gateway or mobile information handling system switches to an optimal WWAN wireless link, an IMSI corresponding to the WWAN wireless link provides for that communication to be on a "home" network. This avoids roaming connections. It is understood that roaming connections may be more expensive to operate on a wireless service provider. Additionally, roaming connections may be substantially less efficient. In some cases, a roaming connection from a home network of an IMSI must be routed back to a home network link with the desired alternative wireless service provider. This can require additional communication links to achieve. A direct connection via an access to a home wireless network may be more efficient and less costly. Thus, selecting or switching between optimal wireless service providers by switching IMSIs may yield cost savings on a cost per gigabyte basis.

It is understood that cost per gigabyte may also vary between wireless links available from the list of optimal wireless links determined via a context aware radio resource management system as described herein. Cost per gigabyte on wireless service carriers may vary among WWAN links. For example, a vehicle travelling across borders may be subject to substantial cost fluctuations among WWAN carriers. In another example embodiment, some wireless links, such as non-WWAN links may be less expensive as well. Settings for a smart vehicle gateway or a mobile information handling system may serve to prioritize cost per gigabyte based on location when selection from optimal wireless links is made. Moreover, a smart connection manager may select between a plurality of simultaneous wireless links established for a smart vehicle gateway. The basis of selection may be on quality of the links available, traffic levels, or suitability to expected data needs. However, the basis of selection may also be based on a cost per gigabyte basis to select the most cost efficient option when available.

FIG. 3 illustrates a context aware radio resource management method for use in selecting a network and technology within wireless network 100 at a given location. Several factors are assessed by the context aware radio resource management method in selecting a radio technology and a service provider. A software agent is deployed at a mobile information handling system or elsewhere in the network for executing the context aware radio resource management method. In one example embodiment, the context aware radio resource manager may reside at a smart vehicle gateway such as 135 and may interface with the cloud based context aware resource management system server such as 190. At step 310, the context aware radio resource management system software agent obtains user profile data. The user profile data establishes an approximate cyclostationary usage pattern of the mobile information handling system. The time of day, location, types of usage, and usage percentages during a sample time interval are example factors included in the user profile data. This user profile data also may include a confidence of the estimate. This may be a statistical measurement of a mean and standard deviation for a set of data. Alternatively, the confidence of estimate may involve a goodness of fit metric to an expected set of values. Alternative statistical analysis may be performed on the user profile data to provide a confidence of the estimate. In the context of a smart vehicle gateway, a smart connection manager operating some or all of a context aware radio resource management system may obtain user profile data for the smart vehicle gateway 311. In some embodiments, the smart connection manager of the context aware radio resource management system may obtain user profile data for mobile computing devices within the vehicle 312 and for IoT devices and sensors 313.

At step 320, the context aware radio resource management system receives wireless link radio frequency broadband traffic reports. For location and time, available radio technologies and service providers are listed. The reports contain data relating to location, time and a radio frequency profile of given radio technologies for the available service providers. The data may also include an associated confidence of estimate. The wireless link radio frequency profile may combine recent reports, historical traffic reports, as well as data measured via an active device radio frequency scan. In some embodiments, in order to minimize mobile information handling system battery power consumed, radio frequency broadband traffic reports from the network may only be requested or sent when a service provider network or a mobile information handling system detects a significant change in signal quality or the network broker server detects that the local crowd source information is out of date.

The context aware radio resource management system receives battery power level data at step 330 from an intelligent battery management system of the mobile information handling system. The battery power level input may determine that certain wireless communication protocols are too costly in terms of power. Below a defined battery level threshold, the context aware radio resource management system may disable the most advanced protocols to save energy. For example, with only 10% battery power remaining, the context aware system may recommend to a user to disable high power consuming protocols such as 4G. The option may be given to the user, or automatic shut down of the radio frequency subsystem may take place. In a further example, the context aware system may recommend or shut down 3.5G at 5% remaining battery power. Any threshold levels may be set to trigger recommended shut down. This data provides the context aware radio resource management system with an ability to manage the mobile information handling system power consumption when battery levels are low. The context aware radio resource management system may switch wireless protocols being when receiving a shut down recommendation. The switching may happen with a continuous connection to the same service provider.

The intelligent battery power management may also determine which services or protocols are unavailable at a given location. This information may come in part from radio frequency profile data in the radio frequency broadband traffic reports. In that case, the radio frequency subsystem transmitters, receivers, and controllers associated with unavailable protocols may be turned off by the context aware radio resource management system. For example, if no 4G WWAN is detected, the radios capable of communicating with these protocols may be turned off in the mobile information handling system. As before, the option may be recommended to the user of the mobile information handling system before shutting a subsystem down.

Step 340 depicts that a variation of the mobile wireless traffic reports may be used by the context aware radio resource management system. This variation is a link energy consumption report. These energy link reports contain data relating to time, location and radio frequency profile information similar to the radio frequency broadband traffic reports 320. In addition, measurements of energy consumed during use of a specified wireless link for a specified wireless service type is reported in the energy link reports 340. The energy link data profile matrix can provide more detailed information above the mobile wireless link radio frequency traffic reports. As with other input factors, a confidence of estimate associated with this data may be included. The energy link report data may combine recent energy link profiles, historical energy link reports, and measurements through mobile information handling system scans during operation.

At method step 350, the context aware radio resource management system receives the user profile data 310, the wireless link radio frequency broadband traffic reports 320, and battery power level data 330. Alternatively, the energy link reports 340 may be received as a variation of the wireless link radio frequency broadband traffic reports 320. These inputs are assessed by the context aware radio resource management system software, such as in connection with a smart connection manager for the smart vehicle gateway, at 350. The context aware radio resource management system software determines the optimal radio frequency technology protocol and service provider to be used. This determination is based, at least in part, on some subset of data in the input reports. Also, the settings such as what protocols are available, which protocols have been shut down, or what power is required to transmit on a given protocol are determined for the mobile information handling system. Again, optimal refers to those devices which meet several threshold criteria determined by the context aware radio resource management system.

In one embodiment, the wireless link assessment 350 may result in a ranked list of service providers that are optimal due to meeting various requirements. Using user profile reports 310 and radio frequency link reports 320, each service provider may be given an overall rank as follows:

Service Provider Rating (j)=$\Sigma_{i=1 \ to \ k}$(User Profile by Technology*Link Rating), where i=a technology index, j=service provider index, and k=the number of wireless technologies.

The service providers can be ranked by this score. For a matrix of link protocols=[2G, 2.5G, 3G, 3.5G, 4G], an example user profile by technology may result in the following matrix (30%, 25%, 15%, 30%, 0%). The user profile shows the anticipated protocol usage score from a location and time period. A Link Rating (j) may result in the following matrix (70%, 80%, 95%, 90%, 30%). The link rating shows a quality of service score by protocol for a service provider at a location and time. The service provider rating for a user profile in this example would result in 0.8225. Altering the weight of factors may increase or decrease the relevance of certain protocols depending on the change to the calculations. Either the user profile scores or the link ratings may change the calculations of the scores assigned there. This is described further below. The above values serve only as an example.

Battery power levels 330, energy link reports 340, and additional factors, such as subscriber cost of wireless link usage, may also be assessed to select a wireless link. Subscriber cost or settings may influence the determination by weighting protocol options and influence the scoring described below. Alternatively, settings or subscriber cost may be used to mask out protocol options altogether.

The selection of a wireless link by the context aware radio resource management system may depend on the factors and settings described above. For example, if optimal speed of connection is the goal with less consideration of power consumption, the weight assigned by the context aware system to input data may be influenced. This may be the case if the context aware resource management system detects a connection to an AC power source. User profile data 310 showing usage and the wireless link radio frequency broadband traffic reports 320 indicating link quality and capacity will be more heavily weighted. Energy consumption data may be less heavily weighed. If on the other hand, lower power consumption and long battery life are optimal considerations, battery power level data 330 and the energy link reports 340 may be more heavily weighted. Any combination of weighting involving anticipated usage, radio frequency channel quality, battery power levels, or efficient power consumption may be used in the present embodiment.

Upon determination of an optimal link or links, the context aware radio resource management system provides a command to select a preferred wireless link protocol and service provider. In an alternative embodiment, a list is created providing a preferred set of wireless links and protocols. The context aware radio resource management system may also list wireless links in rank order as described above.

Turning to 355, a smart connection manager may determine from the context aware radio resource management system list for a selected wireless service carrier link protocol for an optimal wireless link protocol. With the weighted list, the smart connection manager may determine a preferred service provider and protocols for the location of the smart vehicle gateway. The smart connection manager may then issue a command to the eSIM of the smart vehicle gateway to select an IMSI corresponding with the selected wireless service carrier as a home network. In doing so, the smart vehicle gateway may avoid roaming while selecting an optimal wireless link for communication by the vehicle mobile information handling systems or IoT devices.

At method step 360, a request is made for access to the selected network. The context aware radio resource management system transmits a command to the selected wireless link provider for the desired protocol. The smart vehicle gateway uses the context aware radio resource management system list to command to an application processor controlling eSIM profile selection within the smart vehicle gateway. The command to the eSIM will adjust the IMSI under which the wireless adapter is operating when it is desired to switch wireless service carriers. Then the wireless adapter negotiates access to the preferred service provider and selects a protocol.

At step 370, if the access request is accepted by the service provider, the mobile information handling system is connected to the selected service provider and wireless protocol. If access is declined, the wireless adapter will request access to another preferred protocol at the service provider. It that still does not succeed, then the smart connection manager may command the eSIM to switch to a different IMSI for another wireless service provider in the weighted list received from the context aware radio resource management system. If the list is in rank order, then one embodiment the smart connection manager may turn to each next-ranked protocol and service provider in order on the list. This repeats until a satisfactory optimal wireless link is found and access made for the mobile information handling system.

Figure 4:
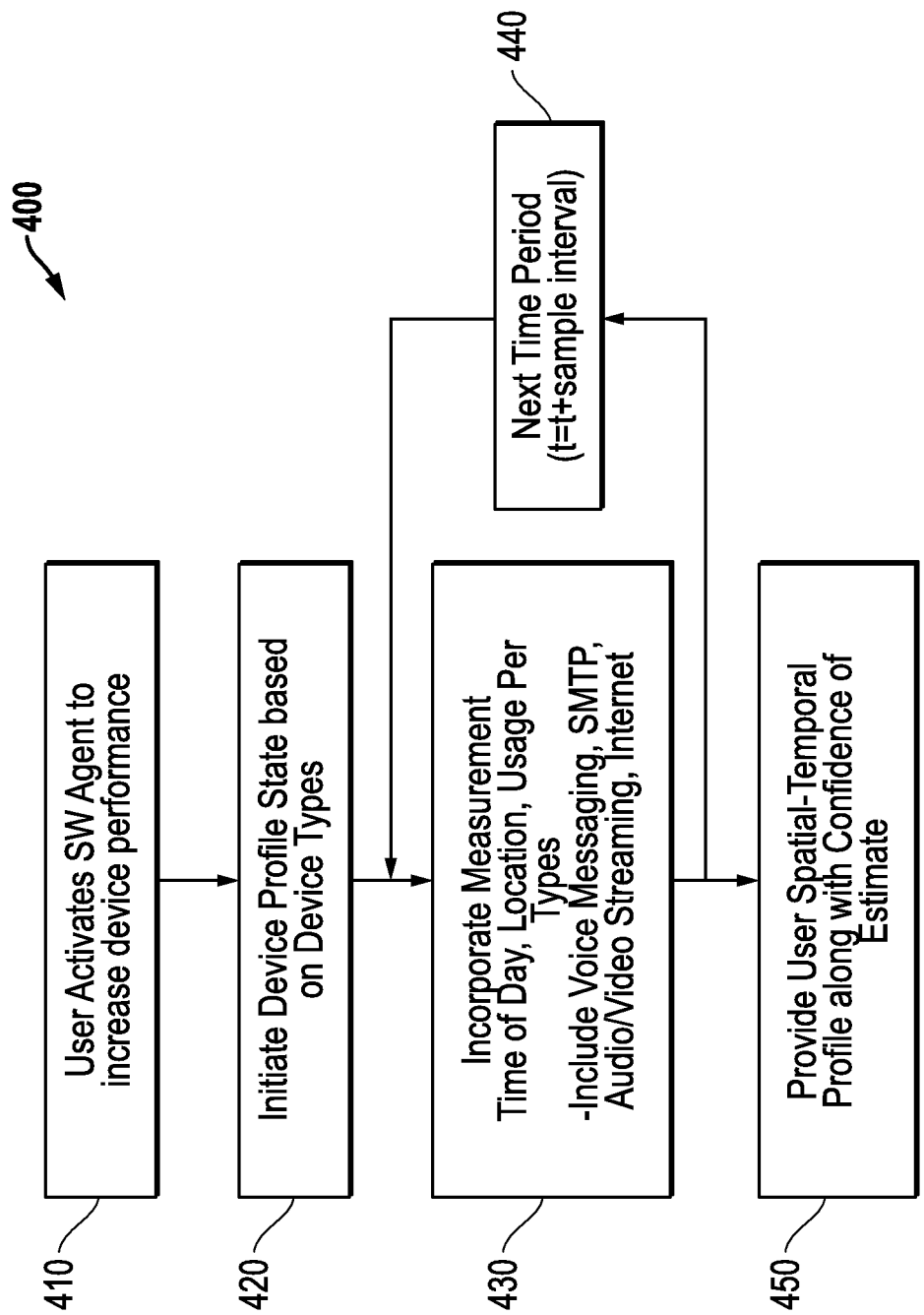
FIG. 4 is a flow diagram illustrating a method of mobile information handling system usage profiling according to an embodiment of the present disclosure.

FIG. 4 illustrates a method 400 for generating an end-user profile in the context aware radio resource management system. In the first step 410, the context aware radio resource management system software agent is started to optimize device performance in selecting a wireless link. Some or all of the context aware radio resource management may operate at a mobile information handling system or smart vehicle gateway to measure and monitor device data and communication usage. At step 420, the context aware radio resource management system software agent initiates a baseline device profile state. The device profile state reflects expected usage for the mobile information handling system. It includes various usage service types. Example usage types may include voice, audio streaming, video streaming, internet usage, email communication, SMS or other messaging. For a smart vehicle gateway, usage types may be impacted by mobile information handling systems and other computing systems within the vehicle. Moreover, the device profile of a smart vehicle gateway will also be impacted by an IoT sensors or other devices that wirelessly transmit through the smart vehicle gateway to establish a usage profile for the smart vehicle gateway. In some embodiments, individual device profiles may also be established for the individual information handling systems or IoT sensors and devices within the vehicle.

A previous user data profile collected for the operation of the mobile information handling system, smart vehicle gateway, or IoT sensors/devices may serve as the baseline device profile for the respective device. Such a profile is specific to the location of the device and to a time slice during which operation is being optimized. Locations may be assigned to geographic zones such as a campus, city, borough, county, etc. Time may be assigned to defined time periods during a day but may differ across days of the week. This zoning and time definition is optional but will help control the number of different user profiles generated.

In one embodiment, a set default user profile may be used as a baseline. For example, the client service profile may assume SMS messaging consumes 10% of device usage, voice communications consume 30%, video streaming consumes 10% of usage, audio streaming consumes 15% of usage, SMTP email consumes 10%, and internet activity consumes 25%. This baseline state may be specific to the mobile information handling system type. For example, the mobile information handling system may be geared toward usage on a certain network protocol. For example, certain systems may be optimized to operate on a 3G or 4G network. Additionally, a default service provider and wireless protocol may generally be assigned to the mobile information handling system. This default wireless link may affect or set the baseline profile state.

At step 430, the context aware radio resource management system may initiate operational measurements according to time of day, location of mobile information handling system, and usage levels for various usage types. The usage data measurements may be taken during sample intervals. For example, during a time period from a specific location zone, the context aware radio resource management system may monitor operation of the mobile information handling system. It will measure the dwell time or use percentage of each type of service. This can include measuring minutes used or number of calls made for voice service. It can measure bytes transferred or number of requests made for video streaming or audio streaming. It may measure the number of messages sent and received or bytes transferred for SMTP, SMS, or similar messaging. The context aware radio resource management system can also measure the data requests and responses or data volumes exchanged in internet accesses. At each sample interval, the available service providers and available wireless link protocols may be determined as well.

The results of the measurements are incorporated into a user profile at step 430. Rather than strictly relying of total data volumes or number of requests, the measurements may be scaled or normalized to reflect a percentage of service usage. This normalized scoring permits comparison. The normalization may be scaled to permit scores of usage reflecting importance or frequency of access to the service types. For example, while audio/video streaming may take a large amount of data, usage may be uncommon. For the same time period, the voice service usage or SMTP messaging may be substantially more frequent but may not transfer as much data volume. Therefore, service recommendations may be better scaled toward frequency of accesses rather than total data throughput volumes. If on the other hand video streaming is a daily occurrence, even if only one request occurs at that time period, then scaling may lean toward total data volume. In this case, normalization scaling in favor of data throughput volume may more accurately reflect the usage.

The use or usage percentage may be measured and scored according to the preferred parameters set in the context aware radio resource management system. It may also be averaged with the baseline default or historical user profile state if so desired. For example, previously measured usage data for a location zone and time period may provide higher data confidence if averaged into measured data.

Measurements may be repeatedly taken in later sample intervals at step 440. Such measurements may be conducted throughout an entire day and over the course of several days or longer. The multiple sample measurements of the mobile information handling system usage comprise a spatial-temporal user profile. The spatial-temporal user profile may have an associated confidence estimate. At step 450, the spatial-temporal user profile and any confidence estimate will be stored either at the mobile information handling system or elsewhere in an available database. The spatial-temporal user profile for the mobile information handling system usage assists in selection of radio frequency links for given times and location zones. The user profile may predict the predominantly used combination of services typical of the mobile information handling system during a time period or from a certain location. The predicted service usage assists in selecting an optimal service provider and radio frequency protocol. The spatial-temporal user profile information will be stored in the mobile information handling system to protect end-user privacy information To apply this data to selection of a wireless service provider and protocol, the usage percentage levels are mapped to service protocols available to a mobile information handling system. The mapping of use percentages to a protocol may involve assigning the use percentage for a service to the lowest power consuming protocol available for a usage type. In other words, the service type usage score is mapped to the technology protocol most efficient for that service type. For example, voice communication usage may be assigned to a 2G protocol whereas audio or video streaming may be assigned to 4G. These energy efficiency rules are stored as part of system parameters. These parameters are used to map services to optimal wireless technology. The parameters may also be adjusted as a function of energy state or battery power levels of the mobile information handling system. The parameters may also be specific to the make or model of the mobile information handling system and its capabilities in processing, memory, radio frequency transmission systems and other features. Similarly, operational capabilities or battery or radiofrequency states of the smart vehicle gateway may impact the parameters assessed by the context aware radio resource management system.

Once the usage levels are measured and scaled according to anticipated importance of data throughput versus frequency of access, the result may score messaging at 20% of usage, voice at 30% of usage, video at 10% of usage, audio at 15% of usage, SMTP at 5% of usage, and internet at 20% of usage. For optimizing minimal power consumption, each service usage is mapped to a service protocol. For example, voice may consume the least power on a 2G network. If 2G cannot accommodate video streaming, it may be eliminated however. The voice score is associated with the most efficient choice available. If video streaming is very infrequent at less than 5%, then elimination of 2G protocol may be disregarded. Should the rare video streaming service request occur, the cost of switching protocols may be worthwhile at that time. Switching protocols may even occur within one service provider to minimize cost of access, negotiation, authentication, and switching with a different service provider.

In the present example, messaging and SMTP email are optimal at 2.5G. The email usage score is then mapped to 2.5G. 3G may consume more power, but also may be determined to provide audio streaming services most efficiently. Thus, the audio streaming usage score is mapped to 3G. Internet access and video streaming may be most efficient in a 4G protocol and thus mapped to this protocol. If 4G is unavailable, then 3.5G may be selected instead if it is the next most efficient protocol level.

The mapping will result in a service profile of protocol technology assigned according to optimal power consumption efficiency for the services anticipated for a mobile information handling system. For example, 2G may be weighted with a value of 30% as optimal for voice usage. 2.5 G may be weighted at 25% as optimal for SMS messaging and SMTP email messaging. 3G may be weighted at 15% as optimal for audio streaming usage. And 3.5G may be weighted at 30% for video streaming and http internet access in the case that 4G is unavailable. For a matrix of link protocols=[2G, 2.5G, 3G, 3.5G, 4G], a user profile by technology may result in the following example matrix (30%, 25%, 15%, 30%, 0%). This spatial-temporal user profile data is then utilized by the context aware radio resource management system alone or in combination with other profile reports shown in FIG. 3 to select a wireless link.

Figure 5:
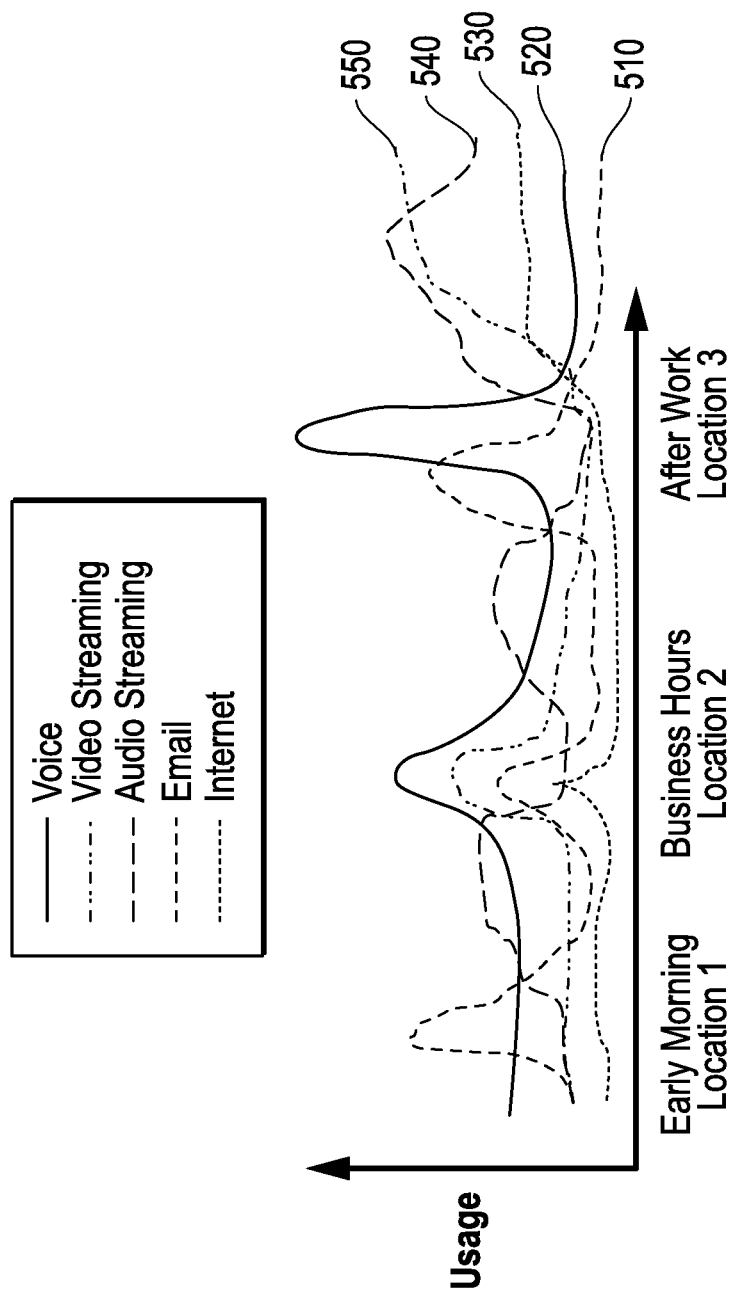
FIG. 5 is a chart illustrating an example usage profile of a mobile information handling system according to an embodiment of the present disclosure.

FIG. 5 illustrates a graphical example of spatial-temporal user trends for a mobile information handling system. As shown in FIG. 5, user trend behavior measurements are shown as a function of time and location. Five usage types are illustrated in this example, voice, video streaming, audio streaming, email, and internet usage. Usage amounts are shown along the x-axis. The y-axis depicts time and various locations. In this example, three locations and time periods are defined, though more or fewer could exist. Those time periods are early morning usage at Location 1, business hours usage at Location 2, and after work hours at Location 3. Each general time period may be comprised of multiple time slices with separate data samples. The mobile information handling system may apply a curve fitting approach to the user profile data to compress information associated with a level of use per type of service per unit of time. An n-order polynomial approach may be used to reduce information to N parameters.

Email usage is depicted in trace 510. Voice bandwidth usage is depicted in trace 520. Internet usage is depicted in trace 530. Audio streaming usage is depicted in trace 540. And video streaming usage is depicted in trace 550. In many cases, the user profile data can be expected to be cyclostationary. In other words, the usage trends repeat themselves. For example, usage may repeat itself daily during a business week. In the example of FIG. 5, voice bandwidth usage 520 increases mid-day during business hours at location 2 during lunch. Voice bandwidth consumption 520 will again increase during after work hours at location 3. This may include increasing during a commute home or upon returning home. Similarly, trends in email usage 510 may show peaks at all three locations with lower bandwidth usage trends arising during non-break business hours at location 2 and late in the evening after work at location 3. Thus, despite variability in these usage schedules, some cyclostationary consistency can be established. For this reason, time period data may be averaged for weekdays or may be specific to Wednesdays depending on the trends. Variability may be accounted for with confidence estimates on the data.

For a smart vehicle gateway as described herein, a graphical example of spatial-temporal user trends may vary significantly depending upon vehicle usage. A fleet vehicle, such as a semi-truck, may be operational and transmitting IoT sensor and device data during business hours. A long haul vehicle such as a cargo train, cargo jet, or trucking vehicle may operate at extended hours overnight in another example. A commuter vehicle on the other hand may have significant wireless communication activity during commute times, but be otherwise limited as to wireless activity between commute times. The graphical example of spatial-temporal user trends of FIG. 5 is but one example.

Figure 6:
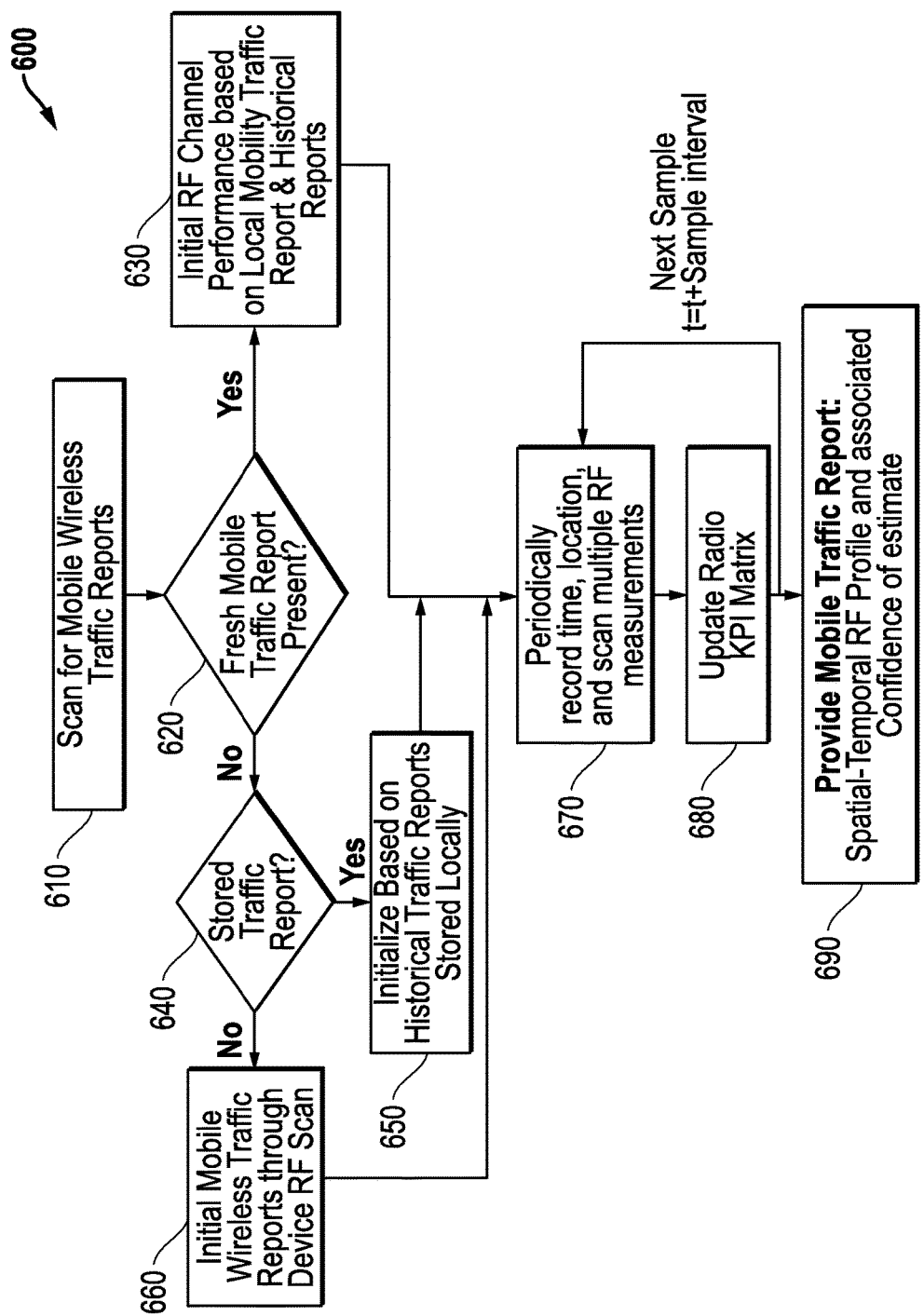
FIG. 6 is a flow diagram illustrating a method for wireless link traffic reporting according to an embodiment of the present disclosure.

FIG. 6 shows a method 600 for establishing a mobile wireless traffic report for a wireless link for wireless links. The mobile wireless traffic report partially comprises a spatial-temporal radio frequency profile for the wireless links. The system begins with a baseline mobile wireless traffic report available from a network broker system or available from cooperative service providers if no previously measured data is available. By way of example, baseline data may be drawn from available wireless coverage maps.

Key performance indicators (KPI) comprise a spatial-temporal radio frequency profile. Data such as received signal strength (RSSI), signal-to-noise ratios (SNR), or signal to interference ratios (SIR) may be relevant channel quality indicators in a KPI matrix. Other data, may include data throughput speeds and communication latencies. One or more of these performance indicators may be used to compute a link rating for a wireless link. Baseline reports rely on estimated values. For example, using baseline estimated received signal strength indicators (RSSI), a link rating may be computed as follows:

Link Rating (i,j)=MAX (MIN (100%, (Estimated RSSI Signal Carrier−Minimum Signal)/Max RSSI signal−Minimum RSSI signal, 0%), where i is a technology index and j is a service provider index.

A maximum RSSI level may be defined in a technology protocol, for example as −70 dBm. The minimum RSSI level may be defined as well, for example at −110 dBm. RSSI is not the only key performance indicator that may be used to compute link ratings. Link rating may be based on different key performance indicator values besides received signal strength. Alternatively, multiple key performance indicator values may be used in the computation of a link rating.

A link rating matrix is established by link protocols for a service provider. For a matrix of [2G, 2.5G, 3G, 3.5G, 4G], the baseline Link Rating (j) computation may result in (70%, 80%, 95%, 90%, 30%). 100% indicates best signal link quality and 0% indicates a signal quality below a minimum acceptable level. The Link Rating (j) evaluates a service provider overall. The context aware radio resource management system may use the link rating scores to evaluate the optimal wireless service providers and available protocols for the anticipated usages. Once a service provider is selected, the context aware radio resource management system may switch between protocols within one service provider depending on changes in usage. Thus, the link rating protocol matrix can assist in selecting a service provider with the best scores in multiple protocols. In another aspect, the smart connection manager of a smart vehicle gateway may select an IMSI, with an embedded wireless service carrier identification, corresponding to a selected service provider. This selection may be based on Link Rating (j) in one embodiment. In another embodiment, the selection may be based a wireless link protocol having a high enough score for inclusion on an optimal wireless link list. The IMSI selection may then be based on which wireless service carrier provides the ranked wireless protocol. The smart connection manager may then direct the eSIM to switch to an IMSI corresponding to one of the optimal wireless service carriers as a "home" network. Thereby, the smart vehicle gateway or other mobile information handling system may avoid roaming and potentially avoiding a network broker system to connect to wireless links for a wireless service carrier.

At block 610, a context aware radio resource management system operating on a mobile information handling system or in a smart vehicle gateway may scan for wireless link mobile wireless traffic reports fitting a time and location zone for operation. Wireless link mobile wireless traffic reports may be retrieved from a central server database, such as context aware radio resource management system server 190, connected to the wireless networks 140 or 150. Alternatively, they may be located elsewhere in a database such as at a network broker server system. The baseline report may be supplemented or superseded by any fresh or historical mobile traffic reports to assist in selecting a service provider and protocol. Recent or historic radio frequency profiles for time period and location zone may be used to update or supplement the wireless link mobile wireless traffic reports. More recent data may be of greater relevance however. For example, the link ratings in a radio frequency profile may utilize recently measured RSSI values instead of estimated values.

Mobile wireless traffic reports are aggregated via crowd sourcing. They may be categorized by location zone and have time and date stamps to identify freshness. Crowd sourcing of information will enhance the availability of accurate data for location zones and times of mobile information handling system operation. For example, if a mobile information handling system makes a request for a fresh mobile wireless traffic report, the central server database may have reports from other mobile information handling systems with recent timestamps. Alternatively, the central server database may make a request for a recent mobile wireless traffic report from mobile information handling systems in the same location. Whether via recent storage in the central database or via a recent request of fresh crowd sourced mobile wireless traffic reports, such a report may avoid the need for the mobile information handling system to conduct a radio frequency scan itself.

Crowd sourcing mobile wireless traffic reports for locations and times provides a higher chance that a current mobile wireless traffic report for a location is available. It also increases the available data points providing greater certainty and reliability of data. Part of the benefit of crowd sourcing may also involve performing a hysteresis analysis on the data coming from multiple mobile information handling systems to determine trends in wireless link selection. When a wireless link is reported having low traffic and good radio frequency conditions, traffic from systems using the context aware radio resource management system will elect that wireless link. If a large part of the crowd of mobile information handling systems begin to pile onto whichever wireless link is reported to have the best available bandwidth, that link will slow down and underperform. The mobile wireless traffic reports account for this by conducting a hysteresis analysis. If a large number of users begin to select this wireless link, then the method for generating mobile wireless traffic reports accounts for this traffic and alters the recommended wireless links. For example, a second best option may be recommended as optimal for traffic and radio frequency conditions instead. Each crowd sourced mobile wireless traffic report identifies its selected link. A count of these selections can be compared to a threshold rate level of selections for a given link. If the rate of selections exceeds the threshold for a link, then the recommendation may be altered.

At block 620, the method determines whether a fresh mobile wireless traffic report is available for the location of the mobile information handling system or smart vehicle gateway. If so, a fresh mobile wireless traffic report is retrieved from a central server database. At 630, the method assesses the fresh mobile wireless traffic reports and any available historical mobile wireless traffic reports. Historical mobile wireless traffic reports may be stored locally for the mobile information handling system or smart vehicle gateway or received from a central server database. Assessment of both fresh and historical data is used to determine one or more optimal wireless links at step 630. The combination of fresh and historical information provides a radio frequency channel performance assessment of the wireless links. While fresh report data may be weighted more, historical data may add additional depth of data. The context aware radio resource management system elects a wireless link based, at least in part, on the radio frequency channel performance profile as described in FIG. 3.

If no fresh mobile wireless traffic reports are available at step 620, the method seeks stored historical mobile wireless traffic reports from the central server database at step 640. Depending upon the age of these historical mobile wireless traffic reports and the estimated confidence associated with that data, the method will establish a radio frequency channel performance profile based on historical mobile wireless traffic reports at step 650. If there are no reliable historical mobile wireless traffic reports recent enough to base an assessment upon, the context aware radio resource management system initiates a mobile information handling system radio frequency scan. This scan collects data regarding possible wireless links at step 660. This radio frequency scan consumes power and processor resources so should be used sparingly, however it provides up-to-date key performance indicators (KPI) for a new radio frequency profile to be used in a mobile wireless traffic report. Based upon this new mobile wireless traffic report, the system provides a wireless link performance profile to be used by the context aware radio resource management system.

Additionally, in some embodiments of the present disclosure, the smart vehicle gateway may operate a context aware radio resource management system and radio frequency profiles for local wireless links within a vehicle. The local wireless links may then be determined based on performance for connections between mobile information handling systems or IoT devices and sensors within the vehicle and the smart vehicle gateway. These radio frequency profiles may be used by the context aware radio resource management system to determine optimal downstream local wireless links for the mobile information handling systems or IoT devices and sensors within the vehicle. Based upon this data, the smart connection manager of the smart vehicle gateway may elect which wireless links to use via its local wireless adapter to communicate within the vehicle.

The scan or test of radio frequency links may be conducted by the context aware radio resource management system. As a first measure, received signal strength and bandwidth availability for a service provider and a protocol are determined. Then a test of radio frequency data capacity is made. This can test upload and download performance for each service provider and protocol. For example, a standard test data volume may be sent via a wireless link to a server location at the service provider. Similarly, a test data volume may be received from a server location by the mobile information handling system via the wireless link. Latency of response, upload and download speed or throughput can then be measured for the service provider and protocol. The data is associated with a location zone and stamped with a time and date. The type of transmitter/receiver or mobile information handling system may also be recorded. This data set provides a wireless link radio frequency profile that may become part of a mobile wireless traffic report. Upon measuring this data for a location, the report may be shared or published by the context aware radio resource management system from the mobile information handling system.

Once a radio frequency channel performance profile is submitted to the context aware radio resource management system and a wireless link selected, the mobile information handling system may periodically scan multiple wireless links or measure the selected wireless link at step 670. The system may conduct testing to determine the capacity of a link during operation. In order to minimize radio communication and use of resources, the network broker may be used to proactively notify a mobile information handling system if a wireless link selection was made using an obsolete crowd-sourced data source. This network broker server system may compare time stamps of crowd-sourced data used for wireless link selection or ranking with current time stamps of network-stored crowd-sourced material.

Testing is similar to the testing described above. Additionally, context aware radio resource management system may assess the quality of the wireless link being used. In addition to the capacity above, metrics such as bit error rate (BER) and signal-to-interference metrics may be assessed. Bit error rate is the ratio of error bits to total bits sent across a wireless link. It is a metric illustrating a signal to noise ratio which can define the quality of a radio connection for a wireless link. A bit error rate may be a comparison of a sent test stream of data by a transmitter with what is received by a receiver. The bit error rate can be tested by a bit error rate tester in software which transmits a known bit pattern to or from the mobile information handling system. Pre-error correction errors are counted. A signal-to-interference ratio may also be measured. Such a measurement is based on the power levels for signal transmission (e.g., per bit) relative to interference levels in the received signal. Packet error rate, signal-to-noise measurement, or other signal quality testing is also contemplated.

At step 680, the periodic wireless link scan updates a wireless key performance indicator (KPI) data matrix stored on the mobile information handling system. The KPI matrix establishes the spatial-temporal radio frequency profile and comprises the data for the mobile wireless traffic report. The updated data is time or date stamped to establish its freshness. The system may repeat the periodic wireless link scans and update the KPI matrix for future intervals of time.

At step 690, the spatial-temporal radio frequency profile of the current mobile wireless traffic report and any associated confidence of estimate may optionally be advertised to the central server database for use by other mobile information handling systems or by devices such as the smart vehicle gateway of the present disclosure. Thus, the mobile information handling system or smart vehicle gateway may provide its contribution to the crowd sourcing data for a time and location of wireless link access. Alternatively, the mobile information handling system or smart vehicle gateway may store the mobile wireless traffic report locally and respond to requests from a central server database for the information.

Figure 7:
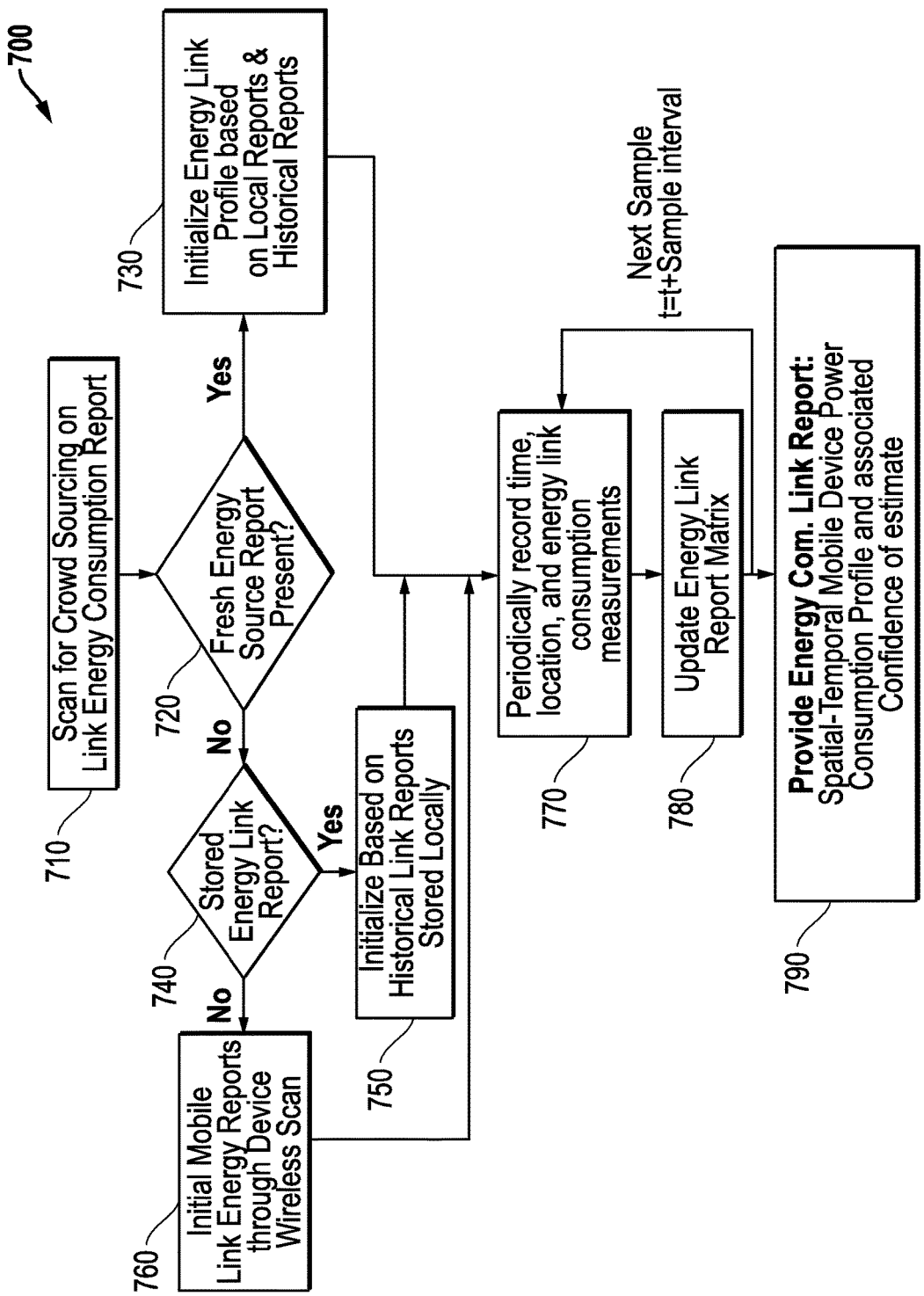
FIG. 7 is a flow diagram illustrating a method for wireless link energy consumption reporting according to an embodiment of the present disclosure.

FIG. 7 shows a method 700 for profiling link energy consumption for wireless communication links. This is an alternative embodiment to the method of FIG. 7 for assessing spatial-temporal radio frequency profiles for wireless links. In addition to assessment of link capacity and quality as in the method of FIG. 6, the system additionally assesses data for device energy consumption relating to various services. In this embodiment, the context aware radio resource management system prepares and delivers an energy link consumption report. The energy link consumption report provides data on power consumed by a mobile information handling system or a smart vehicle gateway while performing certain tasks on a wireless link at a location. Energy link consumption reports contain data indicating how many joules of energy are consumed during sending SMTP emails, sending SMS messages, conducting voice communications, accessing internet services, streaming audio or video, or other uses of mobile information handling systems. This data amounts to another key performance indicator (KPI) in addition to capacity or link quality data for a wireless link. The context aware radio resource management system can measure and utilize some or all data such as link capacity, link quality, and energy consumption in determining preferred wireless links. Link ratings may be calculated similarly to the above description using link energy consumption data. If energy consumption data is unavailable however, the system will function with the mobile wireless traffic reports described in FIG. 6.

Scans for energy consumption information are described further below. The energy link consumption reports retrieved or compiled for the method of FIG. 7 may also record the specific type of information handling system in one embodiment. With a large number of available reports, for example crowd sourced data, filtering for tailored energy consumption information based on a make and model of a mobile information handling system may better account for model-specific variations in wireless operation. As before, the energy link consumption reports are location specific and time specific. Radio frequency scans and energy consumption measurements may consume resources, thus the method begins by searching for available link energy consumption reports.

In step 710, the context aware radio resource management system of a mobile information handling system or smart vehicle gateway may scan for energy link consumption reports for the device and location of operation. The scan searches for fresh, crowd sourced energy link consumption reports among data available from a central server database in the wireless networks 140 and 150 or located elsewhere. As described above, crowd sourcing of energy consumption information will enhance the availability of accurate and current data for locations and times of mobile information handling system operation. A request for a fresh energy link consumption report may be submitted to the central server database or some other database storing such reports. The request may be location specific, time period specific, device specific or any combination of the above. Freshness may be a parameter defined by timestamp data on a report submission. For example, reports submitted for a location on the same day or within the past 24 hours may be qualified as fresh. Any limitation of time on freshness may be used. If a time period during a day is split up on an hourly basis, a fresh report may be one that was submitted within the current or previous hour of the same day. Although a different time period for recent radio frequency traffic in a location may also be used by the present embodiment.

In an alternative embodiment, data and reports may not be stored at a central server database, or only a subset of available data may be stored there. The context aware radio resource management system may make a request for a recent energy link consumption report from similarly situated mobile information handling systems at the same location. This request may come indirectly via a request from the central server. Whether via reports stored in the central database or via a recent request for fresh crowd sourced energy link consumption reports, a scan for pre-existing reports may avoid the need for the mobile information handling system or smart vehicle gateway to conduct an energy consumption survey itself.

Additionally, in some embodiments, the smart vehicle gateway may operate a context aware radio resource management system and maintain energy link consumption reports for local wireless links within a vehicle for connections with mobile information handling systems in a vehicle or IoT devices and sensors within the vehicle. These energy link consumption reports may be used by the context aware radio resource management system to determine optimal downstream local wireless links for the mobile information handling systems or IoT devices and sensors within the vehicle with the smart vehicle gateway.

As with the broadband traffic reports for certain locations, part of the crowd sourcing of energy link consumption report data may also involve performing a hysteresis analysis on the data. Analyzing data from multiple mobile information handling systems may determine trends in wireless link selection happening at a location. If many mobile information handling systems at a location begin to select one preferred wireless link, that link may slow down and underperform. The energy link consumption reports account for this crowding onto a link with the hysteresis analysis. If a large number of users begin to select a given wireless link, then the method for generating energy link consumption reports accounts for this factor. The method may alter which links are recommended or in what order they are recommended.

At block 720, the method may determine that a fresh energy link consumption report is available for the location of the mobile information handling system or smart vehicle gateway. It does so by receiving an acknowledgment or a fresh energy link consumption report from a central server database. At 730, the method assesses the fresh energy link consumption reports. The method may also retrieve and include historical energy link consumption reports, if available. Historical energy link consumption reports may be stored locally for the mobile information handling system or received at the mobile information handling system from a central server database. These historical reports may not meet the freshness limitation, but may prove useful. Although historical reports may not be weighted as heavily as a fresh report, the historical reports may still add value or depth to the data available for a given location and time.

Assessment of energy link consumption reports are used to suggest a wireless link at step 730. If conservation of battery power is a preeminent consideration, a link having the least power consumption for wireless services may be recommended. In embodiments where a weighted list of available links is provided, selection by least-power-consumed on average may be used. The context aware radio resource management system may also utilize user profile information to recommend links based on the most likely used wireless service or combination of services at a location or during a time period. The links having the least power consumption for a heavily used service or services by the mobile information handling system will be recommended.

Least-power-consumed may not always equate with recommending a wireless link with the greatest capacity or quality however. Although less energy consumption often tracks the quality of a link, link quality may vastly improve as greater power is used in transmission. For example, higher power consuming transmission may be used by a transmitter to improve signal to noise ratio and, therefore, more power yields a higher quality link. In this case, the higher power transmission may be preferred. In certain embodiments, detection by a mobile information handling system of the battery state may determine the priority used. In that case, the context aware radio resource management system analyzes the energy link report in combination with a battery power level assessment in determining recommended wireless links. In another alternative, the mobile information handling system may detect connection to an AC power source to set the priority relating to energy link consumption versus radio frequency capacity and quality. Thus, the context aware radio resource management system elects a wireless link based at least in part on the mobile information handling system power consumption assessment and other factors as described in FIG. 3.

If no fresh energy link consumption reports are available at step 720, the method seeks stored historical energy link consumption reports from the central server database at step 740. Depending upon the age of these historical energy link consumption reports and the estimated confidence associated with that data, the method will establish a mobile information handling system power consumption assessment, or that of a smart vehicle gateway, on historical energy link consumption reports stored locally or received locally at step 750. A link may be recommended based upon that report. Similar considerations to the above may be taken into account.

If there are no historical energy link consumption reports recent enough to base an assessment upon, the context aware radio resource management system initiates a mobile information handling system energy link power scan to collect data regarding possible wireless links at step 760. Conducting this energy link power scan consumes power and processor resources, however it provides up-to-date information for a new energy link consumption report. Based upon this new energy link consumption report, the system provides a mobile information handling system power consumption assessment to be used to select a wireless link by the context aware radio resource management system.

A scan or test of radio frequency and energy consumption of links may be conducted by the context aware radio resource management system. Some measures are similar to the method of FIG. 6 to generate a radio frequency link profile. As a first measure, signal strength and bandwidth availability for a service provider and an available protocol is determined. Then a test of radio frequency channel capacity is made. This can test upload and download performance for each service provider and protocol. For example, a standard test data volume may be sent via a wireless link to a server location at the service provider. Similarly, a test data volume may be received from a server location by the mobile information handling system via the wireless link. Latency of response, upload and download speed or throughput can then be measured for the service provider and protocol. In addition, the context aware radio resource management system may measure the energy consumed in transmitting or receiving the test data volume. The power consumed may therefore be expressed in Joules or converted into a Joules/bit or Joules/byte value based on the standard test data volume. The data is associated with a location and time and it is time and date-stamped. The type of transmitter/receiver or mobile information handling system may also be recorded. This energy consumption data may be included in a wireless link radio frequency profile and become part of a mobile wireless traffic report. Upon measuring this data for a location, the report may be shared or published by the context aware radio resource management system from the mobile information handling system.

Once a mobile information handling system power consumption assessment is submitted to the context aware radio resource management system and a wireless link selected, the mobile information handling system may conduct an ongoing mobile information handling system power consumption scan for the wireless link or links being used. Similarly, this power consumption scan may be conducted for a smart vehicle gateway or devices within a vehicle communicating via a smart vehicle gateway. The context aware radio resource management system periodically measures time, location, radio frequency profile data and energy link consumption data for the selected wireless link or links at step 770. The data may be measured during operation of the mobile information handling system. Radio frequency profile measurements such as signal level, capacity, and signal quality may be measured in accordance to the description above for FIG. 6. Power consumption measurements for the mobile information handling system communications on the wireless link are also measured.

Power consumption measurements may be conducted that are specific to the mobile services or data types throughput a smart vehicle gateway used. For example, energy consumption during voice communications may be measured. The amount of power, for example in milliwatts or Joules, may be expressed as a measurement per voice minutes consumed. Power measurements of a radio frequency subsystem from the start of a conversation to the end of a conversation may be measured as described above. The context aware radio resource management system associates this power consumption measurement with the service being utilized. Similarly, for data transferred during internet accesses, power consumption may be measured relative to data volumes uploaded or downloaded. The power would be measured at the active radio frequency subsystem beginning during a download and recording the amount of data or time of a download as well. A power-per-byte or similar measurement may be recorded in an energy link data matrix for that location and time of an internet access. Alternatively, power consumption measurement may be made in terms of number of internet accesses or a combination of accesses and data volumes downloaded or uploaded. Since the power measurements themselves consume power and resources, a sampling of power consumption is more likely. Then estimations of power consumption may be made during operation with a given wireless link for a service type.

In another example, audio or video streaming power consumption may be measured in terms of streaming minutes or data volume. Again, the radio frequency subsystem power consumption may be sampled during the duration of a streaming session and averaged or estimated for the streaming event. The content aware radio resource management system may also measure power consumption levels for SMTP, SMS, or other messaging. This may be done on a per data volume of the messages or based on the number of messages transmitted.

In an aspect, similar power consumption measurements to the above may be made of upstream mobile information handling systems or IoT devices or sensors within a vehicle. These power consumption measurements may be used with a context aware radio resource management system to determine which local wireless links with a smart vehicle gateway may be optimal from a power consumption standpoint for those devices. The power consumption measurements may also be used to determine for each mobile information handling system whether a smart vehicle gateway local wireless link should be used or whether there an external wireless link should be assessed instead.

All of these measurements are then recorded and stored in the radio frequency and power consumption profile as energy link matrix data. This information may be referred to as a link energy consumption report or it may simply be part of a radio frequency profile in a mobile traffic report.

At step 780, the data from the periodic mobile information handling system power consumption scan is updated in an energy link data matrix stored on the mobile information handling system. For the given periodic scan interval, the context aware radio resource management system updates the energy link report matrix in the radio frequency profile. The energy link report matrix establishes the spatial-temporal mobile information handling system power consumption profile. The updated data is time or date stamped to establish its freshness. The system may repeat the periodic mobile information handling system power consumption scans and update the energy link data matrix for future intervals of time. Because measurement scans of this type may be costly in terms of resources and energy consumption, the frequency of such measurements may be limited by the context aware radio resource management system on the mobile device. In one embodiment, depth of wireless link data for statistical purposes at a given location and time may be achieved with crowd sourcing efforts.

At step 790, the spatial-temporal power consumption profile of the mobile information handling system and any associated confidence of estimate may optionally be advertised to the central server database for use by other mobile information handling systems or smart vehicle gateway systems. Thus, the mobile information handling system or smart vehicle gateway may provide its contribution to the crowd sourcing data for a time and location of a wireless link access. Alternatively, the mobile information handling system or smart vehicle gateway may store the mobile wireless traffic report locally. It may optionally respond to requests from a central server database with the radio frequency and wireless link power consumption profile information or reports.

Figure 8A:
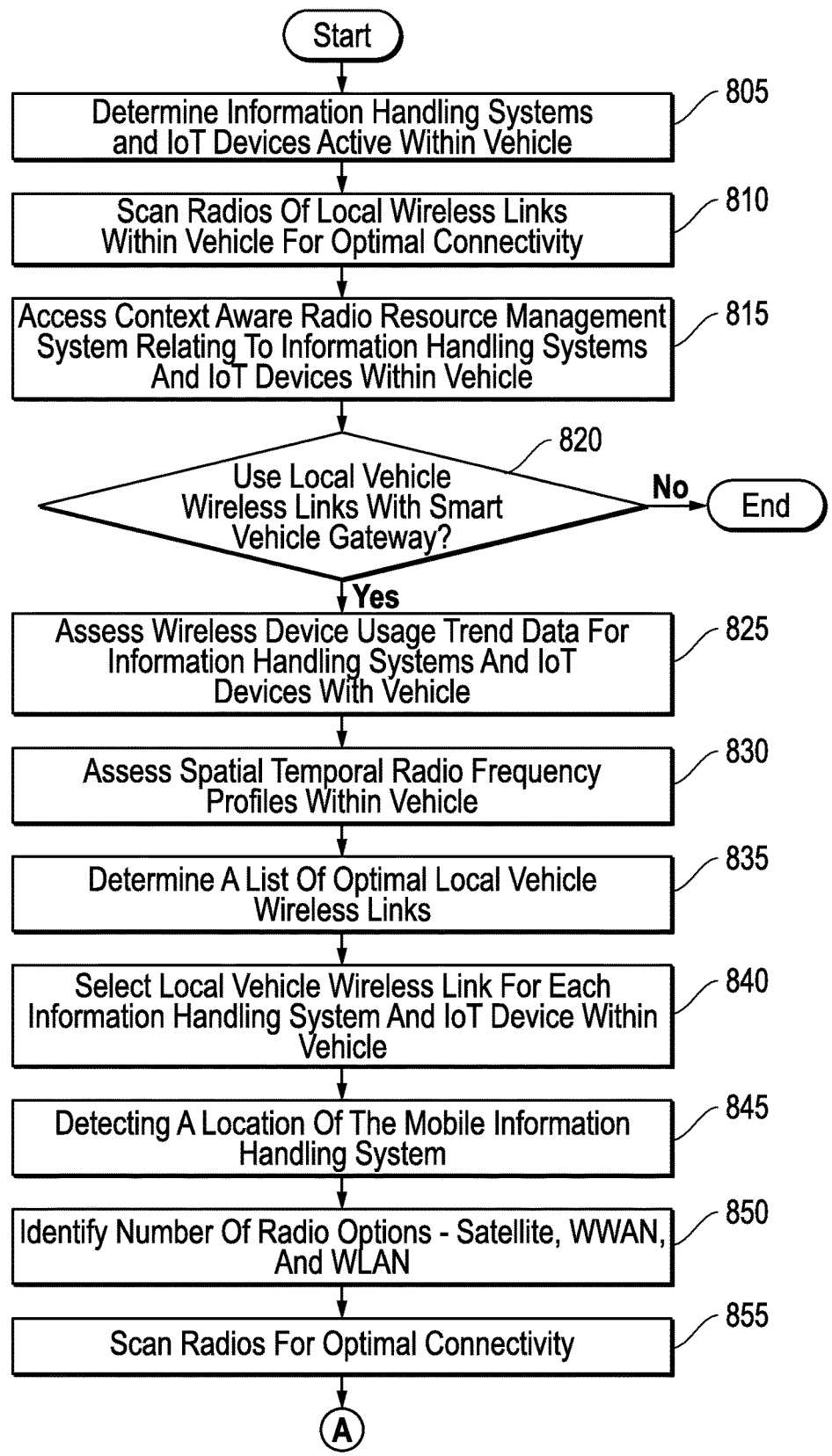
FIG. 8A is a flow diagram illustrating a method of operation of a smart vehicle gateway according to an embodiment of the present disclosure.
Figure 8B:
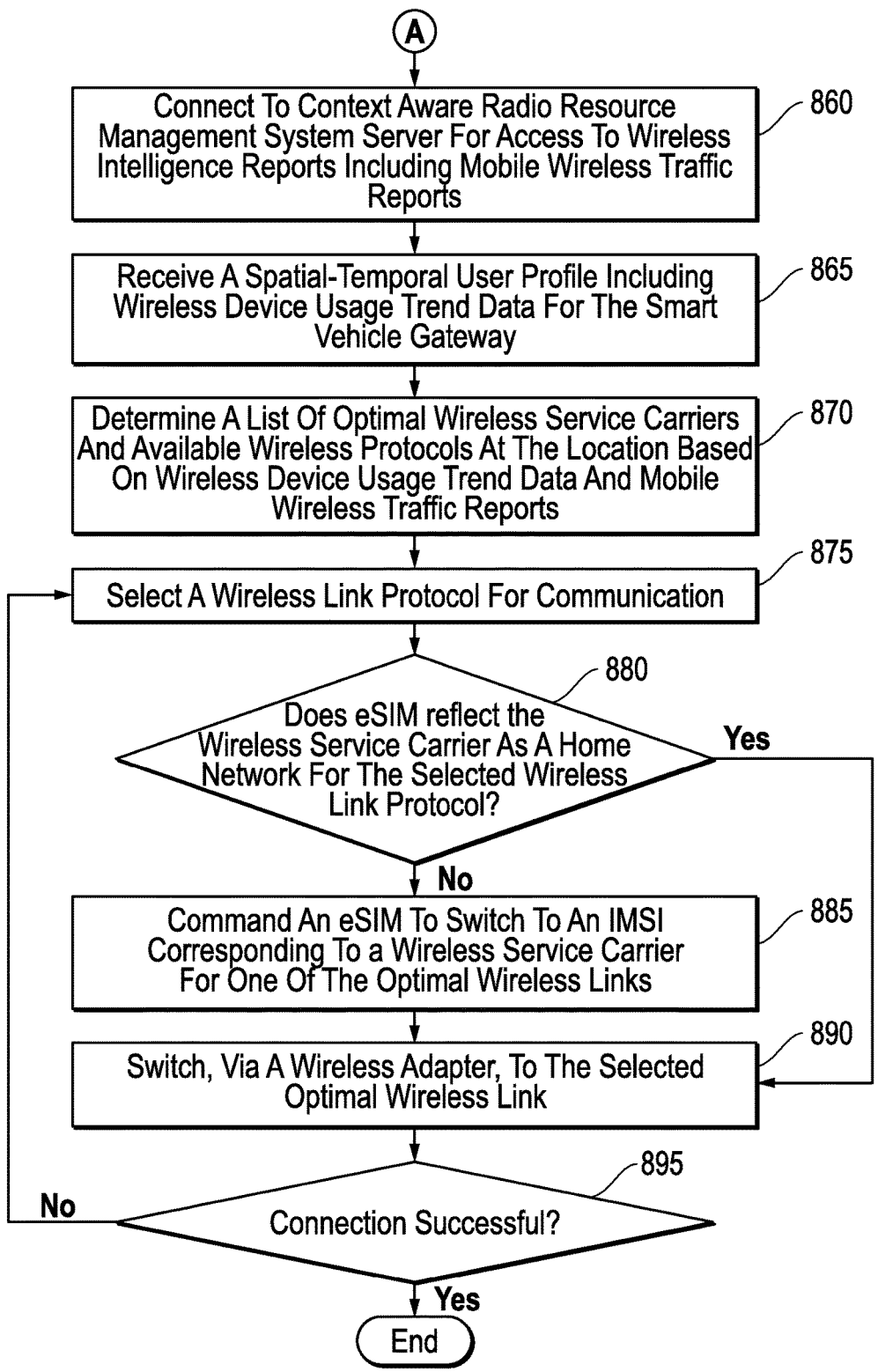
FIG. 8B is a flow diagram illustrating a continuation of the method of operation of a smart vehicle gateway of FIG. 8A according to an embodiment of the present disclosure.

FIGS. 8A and 8B show an example embodiment method for operation of a smart vehicle gateway. The smart vehicle gateway utilizes a context aware radio resource management system. Further, a smart connection manager for the smart vehicle gateway operates with the context aware radio resource management system. The smart connection manager manages the local and upstream-facing wireless adapters for the smart vehicle gateway. The method of FIGS. 8A and 8B begins as 805 where the smart connection manager may determine which mobile information handling systems and IoT devices are functional and operating within a vehicle. Using a local wireless adapter, the smart vehicle gateway may poll the local vehicle mobile information handling systems and IoT devices previously operational within a vehicle. Alternatively, devices may attempt to pair or transmit to the smart vehicle gateway local wireless adapter to indicate activity within the vehicle.

Proceeding to 810, the smart vehicle gateway may scan local wireless links within the vehicle to determine optimal connectivity. An initial scan may determine whether certain local wireless links are available or within working range. For example, a Bluetooth® wireless link may require pairing before it can be used with a mobile information handling system or IoT device. Additionally, the smart vehicle gateway smart connection manager may determine immediate radio frequency conditions or traffic on local wireless links. In some vehicles, such as a freight train or truck, an IoT device or mobile information handling system may be at or beyond a limit of a close range wireless protocol impacting immediate radio frequency conditions. In another example, certain local wireless links may have high traffic volume due to a substantial number of IoT devices or mobile information handling systems transmitting or receiving data or communications.

At 815, the smart connection manager of the smart vehicle gateway may access a context aware radio resource management system either locally or remotely. The wireless device usage trend data and spatial temporal radio frequency profiles may be assessed for the local wireless links with the smart vehicle gateway. In addition, wireless device usage trend data and spatial temporal radio frequency profiles may be assessed for any mobile information handling systems and the IoT devices within the vehicle. The smart connection manager may also receive or determine the quality of direct access options for the mobile information handling systems and IoT devices in the vehicle, if available, with WWAN wireless links or other wireless links.

At 820 based on comparison of various local wireless links with the direct WWAN or WLAN wireless links available to the mobile information handling systems or IoT devices, the smart connection manager determines whether a local wireless link with the smart vehicle gateway is an optimal connection option or whether an external wireless link would be a better option. This determination may, in other embodiments, be made by a context aware radio resource management system at the mobile information handling system or IoT device within the vehicle. If a local vehicle wireless link with the smart vehicle gateway is not to be used, then the process ends for that information handling system or IoT device within the vehicle. If, however, a smart vehicle gateway local link is to be used, the flow proceeds to 825.

The system will assess wireless device usage trend data for the mobile information handling systems and for the IoT devices at 825. The system will also assess spatial temporal radio frequency profiles within the vehicle for local wireless links with the smart vehicle gateway at 830. With this information the smart connection manager software will link with a context aware radio resource management system to determine a list of optimal local vehicle wireless links.

From this above list of optimal local vehicle wireless links, the smart connection manager will select a local vehicle wireless link for each information handling system or IoT device within the vehicle at 840. At this stage, the local wireless adapter of the smart vehicle gateway will be directed to establish one or more local vehicle wireless links accordingly.

The smart connection manager may also coordinate the upstream wireless adapter to establish one or more wireless links with WWAN macro-cellular networks, such as 150 above, or other wireless networks, such as WLAN networks 140 above. The smart connection manager will work in connection with a context aware radio resource management system operating locally, remotely, or some combination thereof. Flow proceeds to 845, where a satellite global positioning system or other position detector for the vehicle is used to determine a location of the smart vehicle gateway. At 850, the smart connection manager determines what radio options are available for communication via wireless links. For example, the smart connection manager may scan the available upstream wireless adapter radios for protocols available. This may include one or more WWAN, WLAN, or satellite radio options. Within a wireless adapter such as a WWAN capable adapter, multiple wireless service carrier networks may be detected as available. If a satellite radio is available, it may be used in some embodiments to establish a high priority connection with a context aware radio resource management system server for access to crowd-sourced RF intelligence reports. In some aspects, a connection with the context aware radio resource management system server for wireless link assessment capabilities may be used if those operations are not conducted locally. In other aspects, the present method may use any wireless connection currently available to establish links to a context aware radio resource management system server instead of a satellite link.

In the example embodiment, flow may proceed to 855. The smart connection manager may also scan the available radio options for optimal radio frequency conditions present in some embodiments to determine an immediate state of various wireless link options. Flow then proceeds to 860 where the context aware radio resource management system provides wireless intelligence reports including mobile wireless traffic reports for historical trends and crowd-sourced data on the wireless state of various wireless link options with a WLAN, wireless service providers and protocols available from those providers. At 865, spatial temporal user profiles including wireless usage trend data for the smart vehicle gateway are also accessed either locally or provided to a remote location for a context aware radio resource management system. In one embodiment, the spatial temporal user profiles including wireless usage trend data for mobile information handling systems and IoT devices within the vehicle will also be assessed by the context aware radio resource management system. The volumes and type of data or communications expected, including how transmission may occur, for the information handling systems and IoT devices operating within the vehicle will impact the optimization scoring of wireless links in an aspect of the present disclosure.

Proceeding to 870, the context aware radio resource management system will make a determination of optimization scoring for the available wireless links in accordance with disclosures herein. Using the context aware radio resource management system resources, a list of optimal wireless link options will be generated. The list will include determination of available WWAN wireless protocols by wireless service carrier as well as other wireless link options, if available. For example, other wireless link options can include WLAN links or satellite links.

The list of optimal wireless service carriers and available wireless protocols will be used to select a wireless link protocol from among the optimal wireless links to establish communication to a WWAN or WLAN. At 875, a smart connection manager or a context aware radio resource management system may select a wireless link protocol for the smart vehicle gateway.

Proceeding to 880, the smart connection manager will determine whether the current state of an eSIM is set to use the selected wireless service carrier as a home network when an optimal WWAN wireless link is selected. An eSIM is a programmable SIM which may change a dedicated IMSI assigned to the wireless adapter of a smart vehicle gateway. The IMSI includes an embedded identity of a wireless service provider to indicate a home network of the subscriber. Thus, by switching between IMSI at an eSIM, a smart connection manager may re-designate a home carrier network for WWAN connections. In this way, the smart connection manager may avoid roaming connections to optimal wireless communication links if they are not part of the current home network indicated for the smart vehicle gateway.

If the eSIM uses an IMSI for a wireless service provider home network that aligns with the wireless service provider of the selected wireless link protocol, then the smart connection manager proceeds to 890 where the smart vehicle gateway wireless adapter is switched to the selected wireless link. If the eSIM uses an IMSI for a different wireless service provider home network from the wireless service provider of the selected wireless link protocol, then the smart connection manager proceeds to 885.

At 885, the smart connection manager determines if the eSIM has available an IMSI corresponding to the selected wireless service provider network. If so, the smart connection manager sends a command to the eSIM to switch the IMSI to one aligned with the selected wireless service provider. Flow then proceeds to 890 where the smart vehicle gateway wireless adapter is switched to the selected wireless link.

At 895, the smart connection manager determines if the connection to the selected optimal wireless link is successful. If not, flow returns to 875 to select a different wireless protocol that may utilize the same or a different wireless service carrier. The process repeats until a successful connection to a wireless link from the list of optimal wireless links is achieved. If the wireless link connection is successful, then the process ends.

Figure 9A:
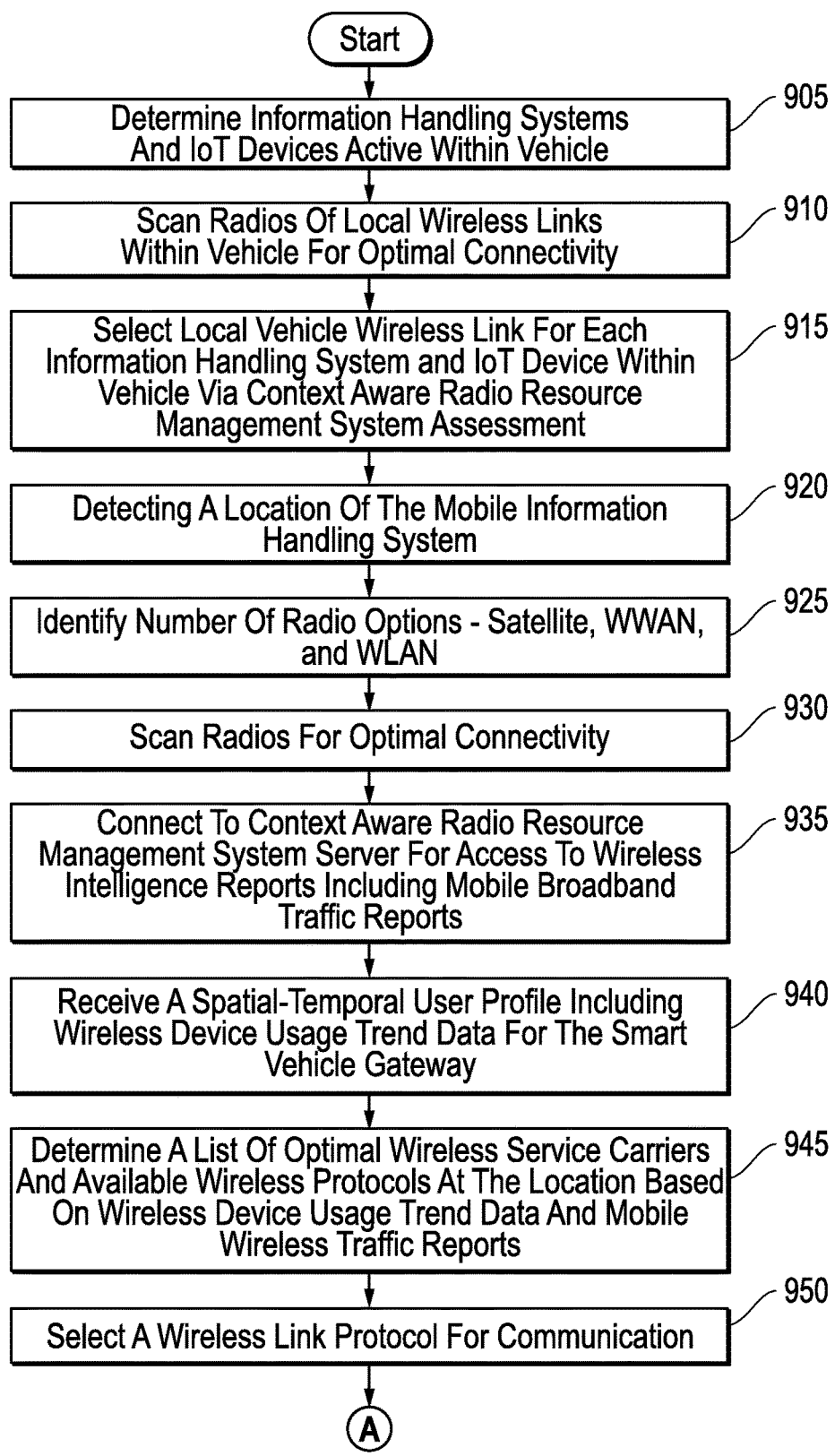
FIG. 9A is another flow diagram illustrating a method of operation of a smart vehicle gateway according to another embodiment of the present disclosure.
Figure 9B:
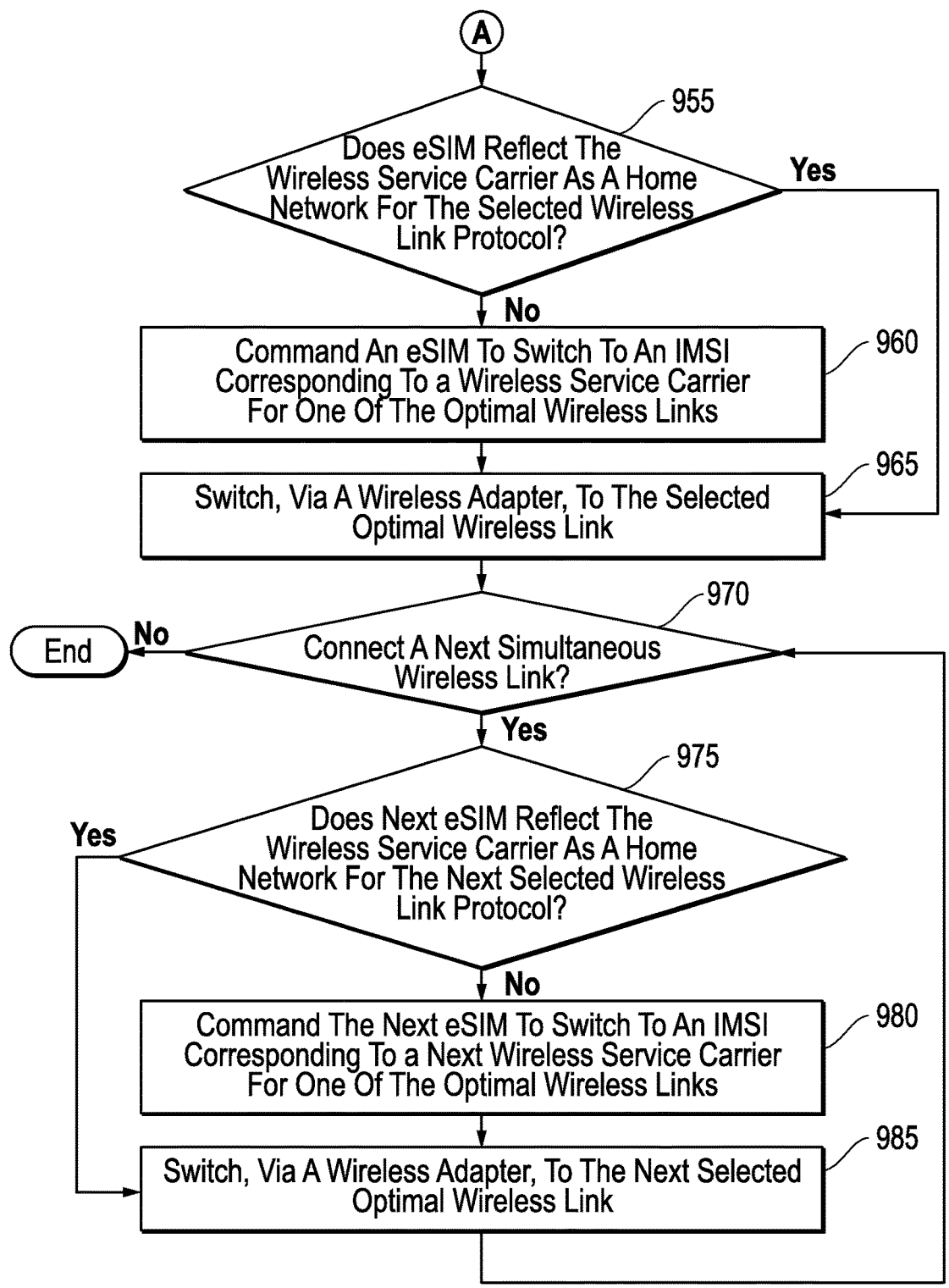
FIG. 9B is a flow diagram illustrating a continuation of the method of operation of a smart vehicle gateway of FIG. 9A according to an embodiment of the present disclosure.

FIGS. 9A and 9B show another example method embodiment for operation of a smart vehicle gateway. In some embodiments, a smart vehicle gateway is set to establish a plurality of wireless links to a WWAN or WLAN for robustness of wireless data communications. As the vehicle travels, a smart connection manager may determine which of the plurality of wireless links to use for data and communications received from the vehicle local network. The robustness of activating redundant wireless links may be beneficial to ensure at least one wireless link is available at a level of QoS and availability to accommodate communications from a smart vehicle gateway.

The smart vehicle gateway operates within a context of a context aware radio resource management system. Thus, the context aware radio resource management system may determine a list of optimal wireless link options from one or more wireless service carriers. The smart connection manager may manage a plurality of wireless adapters or wireless link channels of a wireless adapter in the smart vehicle gateway. Switching between the plurality of upstream-facing wireless adapters may be particularly beneficial since the vehicle travel may differently impact each of the wireless links. As the vehicle travels, the smart connection manager direct communications received from the local vehicle network between simultaneous upstream wireless links. Thus, the smart connection manager may provide continued and efficient wireless linking for information handling systems and IoT devices within the vehicle. Moreover, based on the type of data received from within the vehicle, the smart connection manager may thereby select which simultaneous upstream wireless link on which to forward the data or communication.

The method of FIGS. 9A and 9B begins at 905 where the smart connection manager may determine which mobile information handling systems and IoT devices are functional and operating within a vehicle. Using a local wireless adapter, the smart vehicle gateway may have a processor to execute code or firmware instructions stored there to poll the local vehicle mobile information handling systems and IoT devices previously operational within a vehicle. Alternatively, devices may attempt to pair or transmit to the smart vehicle gateway local wireless adapter to indicate activity within the vehicle.

Proceeding to 910, the smart vehicle gateway may scan local wireless links within the vehicle to determine connectivity. An initial scan may determine whether certain local wireless links are available or within working range for example.

At 915, the smart connection manager of the smart vehicle gateway may access a context aware radio resource management system either locally or remotely. The wireless device usage trend data and spatial temporal radio frequency profiles may be assessed for the local wireless links with the smart vehicle gateway. This includes usage trend data and spatial temporal radio frequency profiles for the mobile information handling systems and the IoT devices within the vehicle. With this information the smart connection manager software determines a list of optimal local vehicle wireless links. The smart connection manager will select a local vehicle wireless link for each information handling system within the vehicle from the list of optimal local vehicle wireless links. A context aware radio resource management system operating at the smart vehicle gateway may provide link ratings for the local vehicle wireless links. Similarly, the smart connection manager will select optimal local vehicle wireless links for each IoT device, including sensors, within the vehicle. At this stage, the local wireless adapter of the smart vehicle gateway will be directed to establish one or more local vehicle wireless links accordingly.

The smart connection manager will also coordinate one or more upstream wireless adapters to establish one or more wireless links with WWAN macro-cellular networks, such as 150 above, or other wireless networks, such as WLAN networks 140 above. Flow proceeds to 920, where a satellite global positioning system or other position detector for the vehicle is used to determine a location of the smart vehicle gateway. The smart connection manager determines what radio options are available for upstream communication via wireless links at 925. Multiple wireless service carrier networks may be detected as available to the smart vehicle gateway wireless adapter. For example, the smart connection manager may scan the available upstream wireless adapter radios for available wireless link protocols. This may include one or more WWAN, WLAN, or satellite radio options.

If a satellite radio is available, it may be used in some embodiments to establish a high priority connection with a context aware radio resource management system server for access to crowd-sourced RF intelligence reports and wireless link assessment capabilities. The context aware radio resource management system may also operate in whole or in part locally at the smart vehicle gateway instead of at a remote server. In other aspects, the present method may use any wireless connection currently available to establish links to a context aware radio resource management system server instead.

Flow may proceed to 930 where the smart connection manager may also scan the available upstream radio options for optimal radio frequency conditions present to determine an immediate state of various wireless links.

Flow then proceeds to 935 where the context aware radio resource management system provides wireless intelligence reports including mobile wireless traffic reports for historical trends and crowd-sourced data on the wireless state of various wireless link options with a WLAN, wireless service providers and protocols available from those providers. At 940, spatial temporal user profiles, including wireless usage trend data for the smart vehicle gateway, are also accessed either locally or provided to a remote location for a context aware radio resource management system.

In another embodiment, the spatial temporal user profiles including wireless usage trend data for detected mobile information handling systems and IoT devices within the vehicle will also be assessed by the context aware radio resource management system as part of the assessment of wireless links for the smart vehicle gateway. The volumes and type of data or communications expected, including how transmission may occur, for the information handling systems and IoT devices operating within the vehicle will impact the optimization scoring of wireless links in an aspect of the present disclosure.

Proceeding to 945, the context aware radio resource management system will make a determination of optimization scoring for the available wireless links in accordance with disclosures herein. For example, the link rating matrix established according link protocols for various wireless service providers may be established by the context aware radio resource management system. The ratings may indicate signal link quality levels or those that are below a minimum acceptable level. Link rating scores are used to evaluate the optimal wireless service providers and available protocols for the anticipated usages. In this case, anticipated usages may be based on overall wireless device usage trend data of the smart vehicle gateway. In other aspects, anticipated usages of mobile information handling systems and IoT devices detected within a vehicle may also be assessed individually or collectively. Once the service providers are determined according to individual wireless link protocols they support, the smart connection manager within the context aware radio resource management system may switch between wireless service carriers and their protocols depending on changes in usage. Thus, the link rating protocol matrix can assist in selecting a service provider with the best scores in multiple protocols as described further below. The list of optimal wireless links will include determination of available WWAN wireless protocols by wireless service carrier as well as other available wireless link options. For example, other wireless link options can include WLAN links or satellite links.

At 950, a smart connection manager or a context aware radio resource management system may select a wireless link protocol for the smart vehicle gateway. The list of optimal wireless service carriers and available wireless protocols is used to select a wireless link protocol from among the optimal wireless links to establish communication to a WWAN or WLAN.

Proceeding to 955, the smart connection manager determines whether the current state of an eSIM is set to use the selected wireless service carrier as a home network when a WWAN wireless link is selected. The programmable eSIM is used to switch between dedicated IMSI values assigned to the wireless adapter of a smart vehicle gateway. Since the IMSI includes an embedded identity of a wireless service provider to indicate a home network of the subscriber, switching an IMSI at an eSIM will re-designate a home carrier network for WWAN connections. In this way, the smart connection manager may avoid roaming connections to selected optimal wireless communication links.

When an IMSI aligns with the wireless service provider of the selected wireless link protocol, no switching is needed. The smart connection manager proceeds to 965 where the smart vehicle gateway wireless adapter is switched to the selected wireless link. If the eSIM uses an IMSI that is set to a different wireless service provider home network from the wireless service provider of the selected wireless link protocol, then the smart connection manager proceeds to 960. At 960, the smart connection manager determines if the eSIM has the IMSI available corresponding to the selected wireless service provider network. If so, the smart connection manager sends a command to the eSIM to switch the IMSI to one aligned with the selected wireless service provider. Flow then proceeds to 965 where the smart vehicle gateway wireless adapter is switched to the selected wireless link.

At 970, the smart connection manager determines if the smart vehicle gateway system is set to establish multiple wireless link connections from the selected optimal wireless link for connection robustness. It is contemplated that several upstream wireless links to a WWAN or WLAN may be established for the smart vehicle gateway in some embodiments. If no further wireless link communications are intended, the method ends. If, however, an additional simultaneous wireless link needs to be set up, another wireless link is selected from the context aware radio resource management system assessment list of optimal wireless links.

When a next selected wireless link protocol is a WWAN protocol, at 975 a next eSIM is assessed to determine if the wireless service carrier for the next selected wireless link protocol is the home protocol for the IMSI currently active. If the IMSI aligns with the next selected wireless service carrier, the method proceeds to 985 where the smart vehicle gateway is switched to the next selected wireless link protocol. As is understood, multiple wireless adapters may be used for each simultaneously established wireless link. Alternatively, one or more wireless adapters may be capable of supporting multiple wireless links and a plurality of eSIMs. In another aspect, the next wireless link selected may be a wireless link protocol served by the same wireless service carrier as the first eSIM. In this case, both wireless links may be established through an IMSI on one or more wireless adapters supported by the first eSIM instead.

If the IMSI at the next eSIM is not aligned with the wireless service provider of the next selected wireless communication protocol, flow proceeds to 980. At 980, the smart connection manager may send a command to the next eSIM to switch to a corresponding IMSI so that the next selected wireless link is established for the smart vehicle gateway on a home network. In this way, the smart vehicle gateway may avoid roaming connection to selected optimal wireless links when establishing simultaneous wireless links. Flow then returns to 970 and the process repeats until no additional simultaneous wireless links are to be established.

Figure 10A:
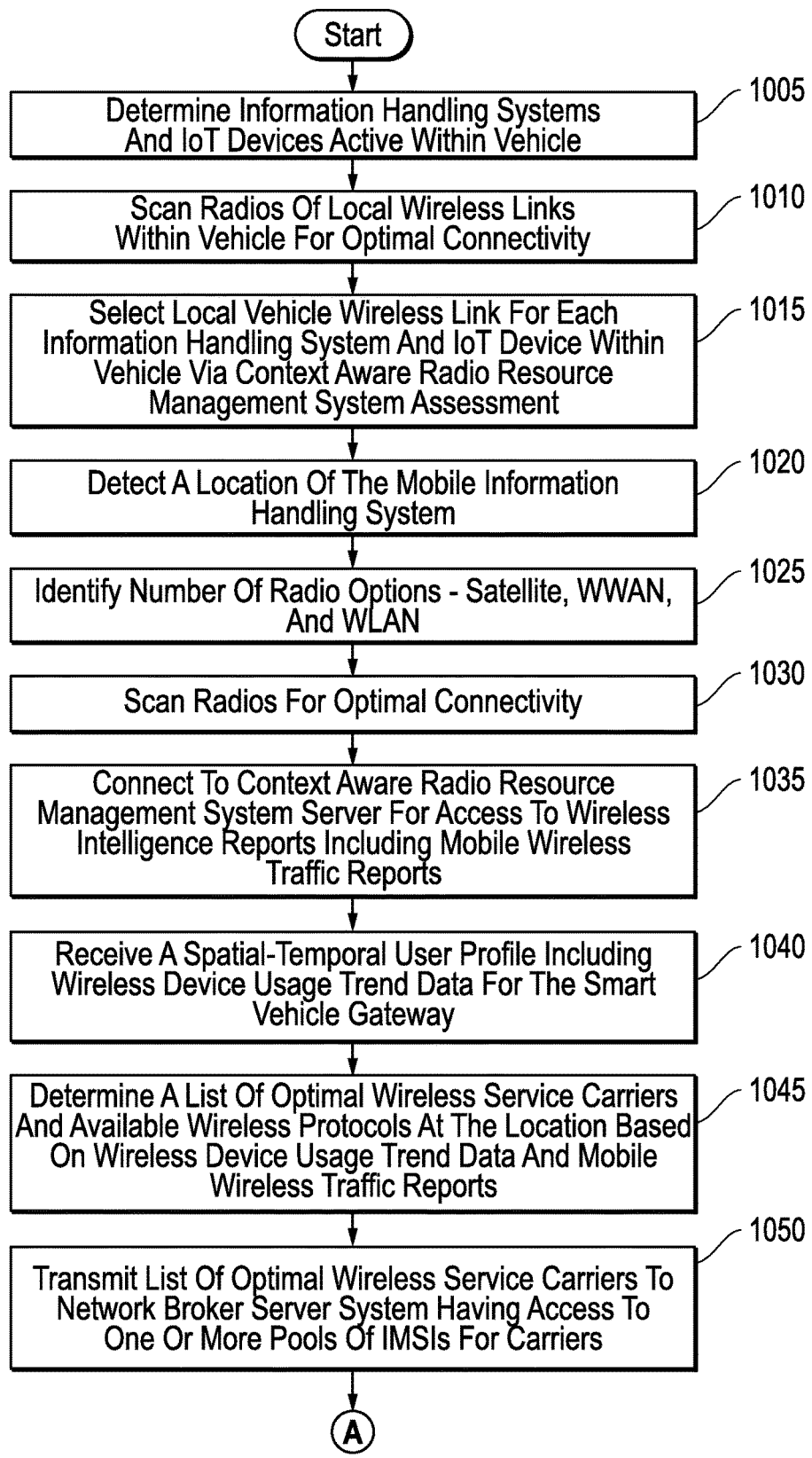
FIG. 10A is yet another flow diagram illustrating a method of operation of a smart vehicle gateway according to yet another embodiment of the present disclosure.
Figure 10B:
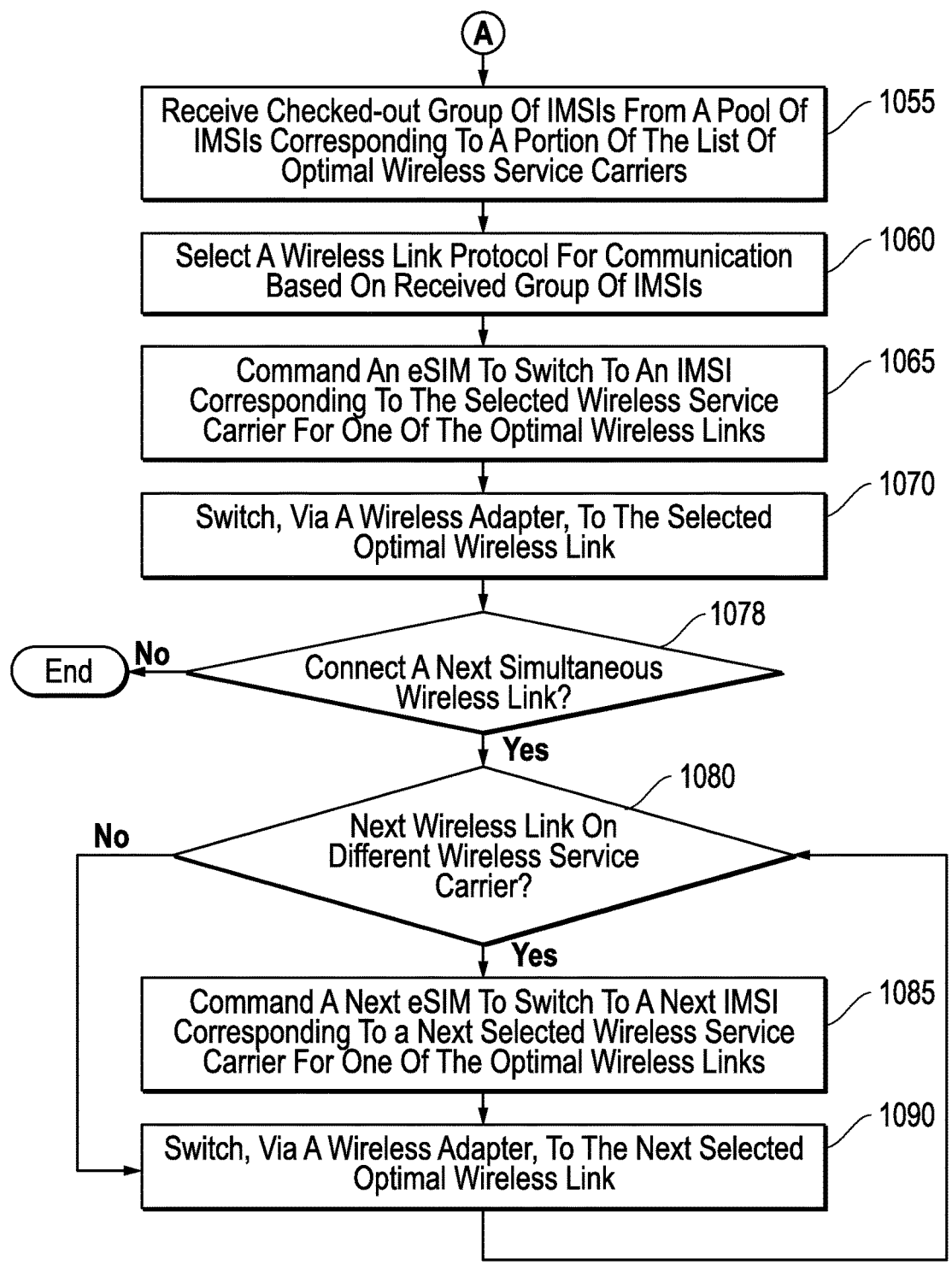
FIG. 10B is a flow diagram illustrating a continuation of the method of operation of a smart vehicle gateway of FIG. 10A according to an embodiment of the present disclosure.

FIGS. 10A and 10B show yet another example method embodiment for operation of a smart vehicle gateway. In some embodiments, when a smart vehicle gateway is set to establish a plurality of wireless links to a WWAN or WLAN for robustness of wireless data communications, the IMSI options may be provided from a network broker system. A network broker system may have pools of IMSIs that may be checked out for a wireless adapter based on its location. The pools of IMSIs at the network broker system may provide access to various wireless service carriers. For example, an IMSI pool may include four wireless service provider IMSI options in an embodiment.

Robustness by activation of redundant wireless links may be beneficial to ensure at least one wireless link is available at a level of QoS and availability to accommodate communications from a smart vehicle gateway. As before, the smart vehicle gateway may operate with a context aware radio resource management system. The context aware radio resource management system may determine a list of optimal wireless link options from one or more wireless service carriers. Having link ratings for the four wireless service providers provides for an ability to transmit an IMSI request to a network broker that screens for only the better rated wireless service provider IMSIs. In this way, fewer IMSIs may be checked out. Those that are checked out from a network broker system may be tailored to the specific needs of smart vehicle gateway or the mobile information handling systems or IoT devices within the vehicle.

The smart connection manager operates with the context aware radio resource management system for managing the plurality of wireless adapters in the smart vehicle gateway. Switching between the plurality of upstream-facing wireless adapters may be particularly beneficial since vehicle travel may differently impact each of the wireless links. Moreover, vehicle travel may alter which group of IMSIs are checked in for a smart vehicle gateway as location changes. As a vehicle travels, a different set of IMSIs from a network broker system pool may be preferable based on context aware radio resource management system analysis.

The method of FIGS. 10A and 10B begins at 1005 where the smart connection manager may determine which mobile information handling systems and IoT devices are operating within a vehicle. The smart vehicle gateway may poll the local vehicle mobile information handling systems and IoT devices previously operational within a vehicle. Alternatively, devices within the vehicle may attempt to pair or transmit to the smart vehicle gateway local wireless adapter to indicate activity within the vehicle.

Proceeding to 1010, the smart vehicle gateway may scan local wireless links within the vehicle to determine optimal connectivity. An initial scan may determine whether certain local wireless links are available or within working range.

At 1015, the smart connection manager of the smart vehicle gateway may access a context aware radio resource management system either locally or remotely. Wireless device usage trend data and spatial temporal radio frequency profiles may be assessed for the local wireless links with the vehicle local network. In some aspects, wireless device usage trend data relating to the mobile information handling systems and IoT devices within the vehicle are determined as well.

With this information the smart connection manager software will link with a context aware radio resource management system to determine a list of optimal local vehicle wireless links. The smart connection manager will select a local vehicle wireless link for each information handling system within the vehicle from the list of optimal local vehicle wireless links. Similarly, the smart connection manager will select optimal local vehicle wireless links for each IoT device/sensor within the vehicle. At this stage, the local wireless adapter of the smart vehicle gateway will be directed to establish one or more local vehicle wireless links accordingly.

Flow proceeds to 1020, where a satellite global positioning system or other position detector for the vehicle is used to determine a location of the smart vehicle gateway. The smart connection manager may manage upstream wireless links including WWAN wireless links based on location. The smart connection manager also determines what radio options are available for communication via wireless links at 1025. For example, the smart connection manager may scan the available upstream wireless adapter radios for protocols available at a location. This may include one or more WWAN, WLAN, or satellite radio options. Within the smart vehicle gateway wireless, multiple wireless service carrier networks may be detected as available. In an example embodiment, flow may proceed to 1030 where the smart connection manager may also scan the available radio options for optimal radio frequency conditions present to determine an immediate state of various wireless links.

At 1035, the smart vehicle gateway connects to a context aware radio resource management system server. If a satellite radio is available, it may be used in some embodiments to establish a high priority connection with a context aware radio resource management system server for access to crowd-sourced RF intelligence reports and wireless link assessment capabilities. The context aware radio resource management system may also operate in whole or in part locally at the smart vehicle gateway instead of at a remote server. In other aspects, the present method may use any wireless connection available to establish links to a context aware radio resource management system server instead.

The context aware radio resource management system provides wireless intelligence reports including mobile wireless traffic reports for historical trends and crowd-sourced data on the wireless state of various wireless link options. The wireless link options may include WLAN link options as well as WWAN wireless service provider network options and various protocols available from those providers. At 1040, spatial temporal user profiles, including wireless usage trend data for the smart vehicle gateway, are also accessed either locally or provided to a remote location for a context aware radio resource management system.

In one aspect of the present disclosure, the spatial temporal user profiles may be accessed or transmitted for the mobile information handling systems and IoT devices within the vehicle as well. The volumes and type of data or communications expected, including how transmission may occur, for the information handling systems and IoT devices operating within the vehicle will impact the optimization scoring of wireless links in these embodiments of the present disclosure.

Proceeding to 1045, the context aware radio resource management system will make a determination of optimization scoring for the available wireless links in accordance with disclosures herein. As previously described, a link rating matrix is established according link protocols for various wireless service providers by the context aware radio resource management system. The link ratings may indicate signal link quality levels or link signals that fall below a minimum acceptable level. Link rating scores are used to evaluate the optimal wireless service providers. The link rating scores are further used to evaluate available protocols from the wireless service carriers for the anticipated usage by the smart vehicle gateway. The context aware radio resource management system will determine a list optimal wireless links. The list will vary and may include wireless link protocol options available from several WWAN wireless service carriers.

At, 1050, smart connection manager will select a subset list of optimal wireless service carriers for access to available wireless protocols. A request is transmitted to a network broker system server including the subset list of selected wireless service carriers. The network broker has to pools of IMSIs, but the IMSI request from the smart vehicle gateway is directed to those ranked by the context aware radio resource management system. For example, if four typical wireless service provider IMSIs are available for checkout from a pool at a network broker system, only two IMSIs associated with service carriers may be requested. The limited request from the smart vehicle gateway is based on list of optimal wireless links determined at the location for the anticipated wireless activity. Thus, not all available IMSIs are checked out from the network broker system by the smart vehicle gateway for use with its one or more eSIMs.

The checked-out subset of IMSIs are received by the smart vehicle gateway at 1055. These checked out IMSIs correspond to wireless service carrier identifications for optimal WWAN wireless link options determined by the context aware radio resource management system.

At 1060, a smart connection manager or a context aware radio resource management system may select an optimal wireless link protocol for the smart vehicle gateway. The list of optimal wireless links will be used to select a wireless link protocol from among the optimal wireless links to establish communication to a WWAN or WLAN. If the selected wireless link protocol is a WWAN wireless link, the selection is made to align with at least one service provider corresponding to the received IMSIs from the network broker system. The IMSIs are received via OTA activation for use with the eSIM at the smart vehicle gateway wireless adapter.

The smart connection manager sends a command to the eSIM to switch the IMSI to one received from the network broker system and aligned with the selected wireless service provider at 1065. In another aspect, the smart connection manager may determine instead that the eSIM is already using the correct IMSI. In the latter case, not IMSI switching will be conducted at the eSIM. Then at 1070, the smart vehicle gateway wireless adapter is switched to the selected wireless link.

The smart connection manager determines if the system is set to establish multiple wireless link connections simultaneously at 1075. If no further wireless link communications are intended, the method ends. If, however, an additional simultaneous wireless link needs to be set up, another wireless link is selected from the list of optimal wireless links. It is contemplated that several upstream wireless links to a WWAN or WLAN may be established for the smart vehicle gateway in some embodiments. The multiple wireless links will be established for connection robustness as previously described. As the vehicle travels, the smart connection manager may direct the smart vehicle gateway to switch between the several upstream wireless links established. Thus, the smart connection manager may provide continued and efficient wireless linking for information handling systems and IoT devices within the vehicle.

The smart connection manager will proceed to 1080 to determine if the next wireless link to be established for the smart vehicle gateway is a WWAN link on a different wireless service carrier. If not, the flow proceeds to 1090 where a channel of the smart vehicle gateway wireless adapter is switched to the next selected wireless link. In some aspects, separate wireless adapters may be used where the smart vehicle gateway switches a next wireless adapter to transmit and receive on the next selected wireless link.

If at 1080 however, the next wireless link to be established is a WWAN link on a different wireless service carrier, the smart connection manager may command a next eSIM associated with a wireless adapter to use the IMSI corresponding to the new wireless service provider. In this way, roaming connections may be avoided improving connection quality and reducing cost of connection. Once the next eSIM has activated the corresponding IMSI, the smart connection manager may switch a wireless adapter to connect with the next selected wireless link. Flow then proceeds back to 1075 to determine whether yet another wireless link is to be established for the smart vehicle gateway. The process repeats until no additional simultaneous wireless links are to be established.

Figure 11:
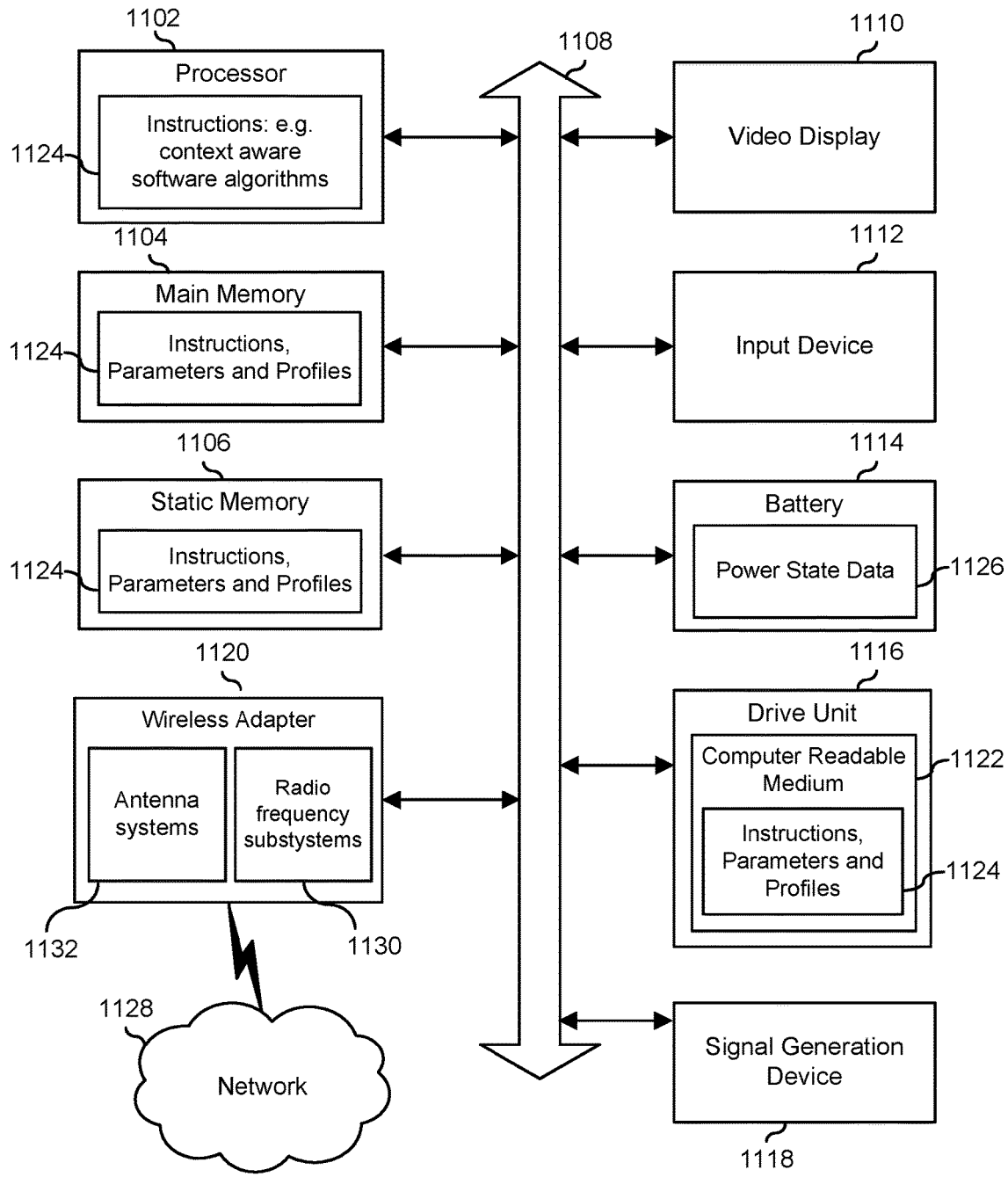
FIG. 11 is a block diagram illustrating an information handling system according to an embodiment of the present disclosure.

FIG. 11 shows an information handling system 1100 capable of administering each of the specific embodiments of the present disclosure. The information handling system 1100 can represent the user information handling systems 110, 120, and 130, the smart vehicle gateway 135, or servers or systems located anywhere within network 100 of FIG. 1, including the remote data center 186 operating virtual machine applications, and the context aware radiofrequency resource management system 190 described herein. The information handling system 1100 may include a processor 1102 such as a central processing unit (CPU), a graphics processing unit (GPU), or both. Moreover, the information handling system 1100 can include a main memory 1104 and a static memory 1107 that can communicate with each other via a bus 1108. As shown, the information handling system 1100 may further include a video display unit 1110, such as a liquid crystal display (LCD), an organic light emitting diode (OLED), a flat panel display, a solid state display, or a cathode ray tube (CRT). Additionally, the information handling system 1100 may include an input device 1112, such as a keyboard, and a cursor control device, such as a mouse. The information handling system may include a power source such as battery 1114 or an A/C power source. The information handling system 1100 can also include a disk drive unit 1116, and a signal generation device 1118, such as a speaker or remote control. The information handling system 1100 can include a network interface device such as a wireless adapter 1120. The information handling system 1100 can represent a server device whose resources can be shared by multiple client devices, or it can represent an individual client device, such as a desktop personal computer, a laptop computer, a tablet computer, or a mobile phone.

The information handling system 1100 can include a set of instructions 1124 that can be executed to cause the computer system to perform any one or more of the methods or computer based functions disclosed herein. For example, instructions 1124 may execute the context aware radio resource management system disclosed herein. In another aspect, instructions 1124 may execute the smart connection manager system disclosed herein for a smart vehicle gateway. In a further example, processor 1102 may conduct processing of wireless service usage by the information handling system 1100 according to the systems and methods disclosed herein. The computer system 1100 may operate as a standalone device or may be connected such as using a network, to other computer systems or peripheral devices.

In a networked deployment, the information handling system 1100 may operate in the capacity of a server or as a client user computer in a server-client user network environment, or as a peer computer system in a peer-to-peer (or distributed) network environment. The information handling system 1100 can also be implemented as or incorporated into various devices, such as a personal computer (PC), a tablet PC, a set-top box (STB), a PDA, a mobile information handling system, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular embodiment, the computer system 1100 can be implemented using electronic devices that provide voice, video or data communication. Further, while a single information handling system 1100 is illustrated, the term "system" shall also be taken to include any collection of systems or sub-systems that individually or jointly execute a set, or multiple sets, of instructions to perform one or more computer functions.

The disk drive unit 1116 may include a computer-readable medium 1122 in which one or more sets of instructions 1124 such as software can be embedded. The disk drive unit 1116 also contains space for data storage. Further, the instructions 1124 may embody one or more of the methods or logic as described herein. For example, instructions relating to the context aware radio resource management software algorithms may be stored here. Additionally, parameters and profiles relating to context aware radio resource management system may be stored here. Parameters may include communication and efficiency rules or data relating to device-specific capabilities. Profiles stored here may include end-user profile data measured by the processor 1102 during wireless service usage processing. Profiles may additionally include crowd source spatial-temporal radio frequency profiles for wireless links or energy link consumption data. In a particular embodiment, the instructions, parameters, and profiles 1124 may reside completely, or at least partially, within the main memory 1104, the static memory 1107, and/or within the processor 1102 during execution by the information handling system 1100. The main memory 1104 and the processor 1102 also may include computer-readable media. Battery 1114 may include a smart battery system that tracks and provides power state data 1126. This power state data may be stored with the instructions, parameters, and profiles 1124 to be used with the systems and methods disclosed herein.

The network interface device shown as wireless adapter 1120 can provide connectivity to a network 1128, e.g., a wide area network (WAN), a local area network (LAN), wireless local area network (WLAN), a wireless personal area network (WPAN), a wireless wide area network (WWAN), or other network. Connectivity may be via wired or wireless connection. One or more wireless adapters 1120 may be implemented including wireless adapters geared to upstream communications or a wireless adapter for local communications via Bluetooth, WiFi, Zigbee or other communication protocols. Wireless adapter 1120 may include one or more radio frequency subsystems 1130 with transmitter/receiver circuitry, wireless controller circuitry, amplifiers and other circuitry for wireless communications. Each radiofrequency subsystem 1130 may communicate with one or more wireless technology protocols. The radiofrequency subsystem 1130 may contain individual subscriber identity module (SIM) profiles for each technology service provider and their available protocols. Alternatively, it may have a software based SIM profile that is reconfigurable, referred to as an electronic SIM or (eSIM). In some embodiments as described herein, a plurality of eSIMs may be used with one or more wireless adapters 1120. The wireless adapter 1120 may also include antenna system 1132 which may be tunable antenna systems for use with the system and methods disclosed herein.

In an alternative embodiment, dedicated hardware implementations such as application specific integrated circuits, programmable logic arrays and other hardware devices can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

The present disclosure contemplates a computer-readable medium that includes instructions, parameters, and profiles 1124 or receives and executes instructions, parameters, and profiles 1124 responsive to a propagated signal; so that a device connected to a network 1128 can communicate voice, video or data over the network 1128. Further, the instructions 1124 may be transmitted or received over the network 1128 via the network interface device or wireless adapter 1120.

Information handling system 1100 includes one or more application programs 1124, and Basic Input/Output System and firmware (BIOS/FW) code 1124. BIOS/FW code 1124 functions to initialize information handling system 1100 on power up, to launch an operating system, and to manage input and output interactions between the operating system and the other elements of information handling system 1100. In a particular embodiment, BIOS/FW code 1124 reside in memory 1104, and include machine-executable code that is executed by processor 1102 to perform various functions of information handling system 1100. In another embodiment (not illustrated), application programs and BIOS/FW code reside in another storage medium of information handling system 1100. For example, application programs and BIOS/FW code can reside in drive 1116, in a ROM (not illustrated) associated with information handling system 1100, in an option-ROM (not illustrated) associated with various devices of information handling system 1100, in storage system 1107, in a storage system (not illustrated) associated with network channel 1120, in another storage medium of information handling system 1100, or a combination thereof. Application programs 1124 and BIOS/FW code 1124 can each be implemented as single programs, or as separate programs carrying out the various features as described herein.

In several of the embodiments in the figures herein it is understood that application programs 1124 and BIOS/FW code 1124 may be used as sets of executable instructions to accomplish the computer implemented methods described in those figures. Each of the figures above is an exemplary embodiment and no order is required to perform the computer implemented method steps recited therein. Furthermore, while the embodiments of the figures above recite several method steps, some or all method steps may be omitted or other different method steps may be added. Additionally, it is understood that combinations and variations on the method steps recited in description of the embodiments for the figures above may be combined in various ways as well.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

In the embodiments described herein, an information handling system includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. For example, an information handling system can be a personal computer, a consumer electronic device, a network server or storage device, a switch router, wireless router, or other network communication device, a network connected device (cellular telephone, tablet device, etc.), or any other suitable device, and can vary in size, shape, performance, price, and functionality. The information handling system can include memory (volatile (e.g. random-access memory, etc.), non-volatile (read-only memory, flash memory etc.) or any combination thereof), one or more processing resources, such as a central processing unit (CPU), a graphics processing unit (GPU), hardware or software control logic, or any combination thereof. Additional components of the information handling system can include one or more storage devices, one or more communications ports for communicating with external devices, as well as, various input and output (I/O) devices, such as a keyboard, a mouse, a video/graphic display, or any combination thereof. The information handling system can also include one or more buses operable to transmit communications between the various hardware components. Portions of an information handling system may themselves be considered information handling systems.

When referred to as a "device," a "module," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCMCIA) card, or other such expansion card), or a system (such as a motherboard, a system-on-a-chip (SoC), or a stand-alone device). The device or module can include software, including firmware embedded at a device, such as a Pentium class or PowerPC™ brand processor, or other such device, or software capable of operating a relevant environment of the information handling system. The device or module can also include a combination of the foregoing examples of hardware or software. Note that an information handling system can include an integrated circuit or a board-level product having portions thereof that can also be any combination of hardware and software.

Devices, modules, resources, or programs that are in communication with one another need not be in continuous communication with each other, unless expressly specified otherwise. In addition, devices, modules, resources, or programs that are in communication with one another can communicate directly or indirectly through one or more intermediaries.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

What is claimed is:

1. An information handling system functioning as a smart vehicle gateway comprising:
   a wireless adapter to communicate with a wireless link;
   a storage device to store a spatial-temporal user profile comprising wireless device usage trend data for a plurality of locations where the smart vehicle gateway has operated;
   a positional detector to detect a location of the smart vehicle gateway;
   an application processor to correlate the wireless device usage trend data to the detected location of the smart vehicle gateway;
   the application processor to determine a list of optimal wireless service carriers and available wireless protocols at the detected location comprising optimal wireless links, the determination based on a mobile wireless traffic report with a spatial-temporal radio frequency profile indicating signal quality for a plurality of wireless links and the wireless device usage trend data for the smart vehicle gateway at the detected location;
   the application processor to select an international mobile subscriber identity (IMSI) for one of the optimal wireless links from an electronic subscriber identity module (eSIM) programmable to switch between multiple available wireless service carriers; and
   the wireless adapter to switch to the selected optimal wireless link on the wireless service carrier corresponding to the selected IMSI.

2. The smart vehicle gateway of claim 1, wherein the optimal wireless service carriers and available wireless protocols are those that meet a minimum threshold of signal quality at the location corresponding to expected communication types according to the wireless device usage trend data.

3. The smart vehicle gateway of claim 1 further comprising:
   the application processor to select a second IMSI for a second optimal wireless link via a second eSIM programmable to switch between multiple available wireless service carriers;
   the wireless adapter to establish the second selected optimal wireless link on a second carrier corresponding to the second selected IMSI.

4. The smart vehicle gateway of claim 1 further comprising:
   a local wireless adapter to wirelessly communicate with a plurality of information handling systems within a vehicle.

5. The smart vehicle gateway of claim 1 further comprising:
   a local wireless adapter to wirelessly communicate with a plurality internet of things (IoT) sensors associated with a vehicle.

6. The smart vehicle gateway of claim 1, wherein the application processor selects the IMSI for one of the optimal wireless links based on a lowest cost per gigabyte from among the optimal wireless service carriers.

7. The smart vehicle gateway of claim 4, wherein the application processor selects the optimal IMSI and switches the corresponding wireless link further based on communication data types to be received from the plurality of information handling systems communicating with the local wireless adapter.

8. A computer implemented method comprising:
   storing a spatial-temporal user profile comprising wireless device usage trend data for a plurality of locations where a smart vehicle gateway has operated;
   detecting, via a positional detector, a position of the smart vehicle gateway;

determining, via an application processor executing code instructions, a list of optimal wireless service carriers and available wireless protocols at the detected location of the smart vehicle gateway comprising optimal wireless links, the determination based on a mobile wireless traffic report with a spatial-temporal radio frequency profile indicating signal quality for a plurality of wireless links and the wireless device usage trend data for the detected location; and selecting, via an electronic subscriber identity module (eSIM), an optimal international mobile subscriber identity (IMSI) corresponding to one of the wireless service carriers for one of the optimal wireless links; and switching, via a wireless adapter, to the selected optimal wireless link corresponding to the optimal IMSI.

9. The computer implemented method of claim 8 further comprising:
wirelessly communicating, via a local wireless adapter of the smart vehicle gateway, with a plurality of information handling systems within a vehicle.

10. The computer implemented method of claim 8, wherein determining the list of optimal wireless service carriers and available wireless protocols at the location is further based on wireless device usage trend data including spatial-temporal user profiles for a plurality of information handling systems within a vehicle.

11. The computer implemented method of claim 8 further comprising:
wirelessly communicating, via a local wireless adapter of the smart vehicle gateway, with a plurality of internet of things (IoT) sensors associated with a vehicle.

12. The computer implemented method of claim 8 further comprising:
establishing a second selected optimal wireless link on a second wireless service carrier corresponding to a second IMSI activated via a second eSIM.

13. The computer implemented method of claim 8 further comprising:
transmitting a request for screened IMSIs based on the list of optimal wireless service carriers from a pool of IMSIs at a network broker system.

14. The computer implemented method of claim 8 further comprising:
selecting the optimal IMSI corresponding to list of optimal wireless service carriers one of the optimal wireless links based on a lowest cost per gigabyte from among the multiple available wireless service carriers.

15. An information handling system functioning as a smart vehicle gateway comprising:
a wireless adapter to communicate with a wireless link;
a local wireless adapter to wirelessly communicate with a plurality of information handling systems within a vehicle;
a storage device to store a spatial-temporal user profile comprising wireless device usage trend data for a plurality of locations where the smart vehicle gateway has operated;
a positional detector to detect a current location of the smart vehicle gateway;
an application processor to correlate the wireless device usage trend data to the detected location of the smart vehicle gateway;
the application processor to determine a list of optimal wireless service carriers and available wireless protocols at the detected location comprising optimal wireless links, the determination based on a mobile wireless traffic report with a spatial-temporal radio frequency profile indicating signal quality for the plurality of available wireless protocols and based on the wireless device usage trend data for the smart vehicle gateway and for the plurality of information handling systems within the vehicle; and
the application processor to select an international mobile subscriber identity (IMSI) for one of the optimal wireless links from an electronic subscriber identity module (eSIM) programmable to switch between multiple available wireless service carriers;
the wireless adapter to switch to the selected optimal wireless link on the selected wireless service carrier corresponding to the selected IMSI.

16. The smart vehicle gateway of claim 15, wherein the optimal wireless service carriers and available wireless protocols are those that meet a minimum threshold of signal quality at the location corresponding to expected communication types according to the wireless device usage trend data.

17. The smart vehicle gateway of claim 15 further comprising:
the wireless adapter to establish a second selected optimal wireless link.

18. The smart vehicle gateway of claim 15 further comprising:
the application processor to select a second IMSI for a second optimal wireless link via a second eSIM programmable to switch between multiple available wireless service carriers; and
the wireless adapter to establish the second selected optimal wireless link on a second carrier corresponding to the second selected IMSI.

19. The smart vehicle gateway of claim 15 further comprising:
the local wireless adapter to wirelessly communicate with a plurality of internet of things (IoT) sensors associated with the vehicle.

20. The smart vehicle gateway of claim 15, wherein the application processor receives a reduced number of IMSIs screened from a pool IMSIs at a network broker system based on the list of optimal wireless service carriers.

* * * * *